US011065321B2

United States Patent
Meyer et al.

(10) Patent No.: US 11,065,321 B2
(45) Date of Patent: Jul. 20, 2021

(54) LIVE ATTENUATED BACTERIAL STRAIN AND ITS USE AS A VACCINE

(71) Applicant: CENTRE DE COOPERATION INTERNATIONALE EN RECHERCHE AGRONOMIQUE POUR LE DEVELOPPEMENT (CIRAD), Paris (FR)

(72) Inventors: Damien Meyer, Guadeloupe (FR); Jonathan Gordon, Leuven (BE); Nathalie Vachiery, Saint Mathieu de Treviers (FR); Dominique Martinez, Sauve (FR)

(73) Assignee: CENTRE DE COOPERATION INTERNATIONALE EN RECHERCHE AGRONOMIQUE POUR LE DEVELOPPEMENT (CIRAD), Paris (FR)

( * ) Notice: Subject to any disclaimer, the term of this patent is extended or adjusted under 35 U.S.C. 154(b) by 0 days.

(21) Appl. No.: 16/648,583

(22) PCT Filed: Sep. 21, 2018

(86) PCT No.: PCT/EP2018/075634
§ 371 (c)(1),
(2) Date: Mar. 18, 2020

(87) PCT Pub. No.: WO2019/057909
PCT Pub. Date: Mar. 28, 2019

(65) Prior Publication Data
US 2020/0215172 A1 Jul. 9, 2020

(30) Foreign Application Priority Data
Sep. 21, 2017 (EP) .................. 17306235.7

(51) Int. Cl.
A61K 39/00 (2006.01)
A61K 48/00 (2006.01)
A01N 63/00 (2020.01)
A61K 39/02 (2006.01)

(52) U.S. Cl.
CPC .... *A61K 39/0233* (2013.01); *A61K 2039/522* (2013.01)

(58) Field of Classification Search
CPC ......... A61K 39/00; A61K 48/00; A01N 63/00
USPC ........ 424/9.1, 9.2, 93.2, 93.4, 184.1, 197.11, 424/234.1
See application file for complete search history.

(56) References Cited

U.S. PATENT DOCUMENTS

2016/0206720 A1 7/2016 Purtle et al.

FOREIGN PATENT DOCUMENTS

WO 2009/034575 A1 3/2009

OTHER PUBLICATIONS

Wang, D., et al. Applied and Enironmental Microbiology, 2013, vol. 79, No. 23, pp. 7150-7150.*
International Search Report dated Oct. 23, 2018, issued in corresponding International Application No. PCT/EP2018/075634, filed Sep. 21, 2018, 3 pages.
Written Opinion of the International Searching Authority dated Oct. 23, 2018, issued in corresponding International Application No. PCT/EP2018/075634, filed Sep. 21, 2018, 6 pages.
Mingqun, L., et al., "Analysis of complete genome sequence and major surface antigens of Neorickettsia helminthoeca, causative agent of salmon poisoning disease," Microbial Biotechnology 10(4):933-957, Jun. 6, 2017.
Atack, J. M., et al., "Characterization of an ntrX Mutant of Neisseria gonorrhoeae Reveals a Response Regulator That Controls Expression of Respiratory Enzymes in Oxidase-Positive Proteobacteria," Journal of Bacteriology 195(11):2632-2641, Apr. 5, 2013.
Marcelino, I., et al., "Comparative Proteomic Profiling of Ehrlichia ruminantium Pathogenic Strain and Its High-Passaged Attenuated Strain Reveals Virulence and Attenuation-Associated Proteins," PLOS ONE 10(12), Dec. 21, 2015, 23 pages.
Mcbride, J.W., et al., "Molecular and cellular pathobiology of Ehrlichia infection: targets for new therapeutics and Immunomodulation strategies," Expert Reviews in Molecular Medicine, vol. 13, Oct. 1, 2011, 24 pages.
Faburay, B. J. Y., "Molecular epidemiology of heartwater (Ehrlichia ruminantium infection) in The Gambia," Jan. 1, 2011, retrieved from the Internet Nov. 16, 2017 <https://www.researchgate.net/profile/Bonto_Faburay/publication/46687069_Molecular_epidemiology_of_heartwater_Ehrlichia_ruminantium_infection_in_The_Gambia/links/00463524b6699d36eb000000/Molecular-epidemiology-of-heartwater-Ehrlichia-ruminantium-infection-in-The-Gambia.pdf>, 155 pages.
International Preliminary Report on Patentability, dated Mar. 24, 2020, issued in corresponding International Application No. PCT/EP2018/075634, filed Sep. 21, 2018, 7 pages.

* cited by examiner

*Primary Examiner* — Rodney P Swartz
(74) *Attorney, Agent, or Firm* — Christensen O'Connor Johnson Kindness PLLC

(57) ABSTRACT

Embodiments of the present disclosure relate to a vaccine composition comprising a bacterial strain with a deleted or inactive ntrX gene.

Figure 1:
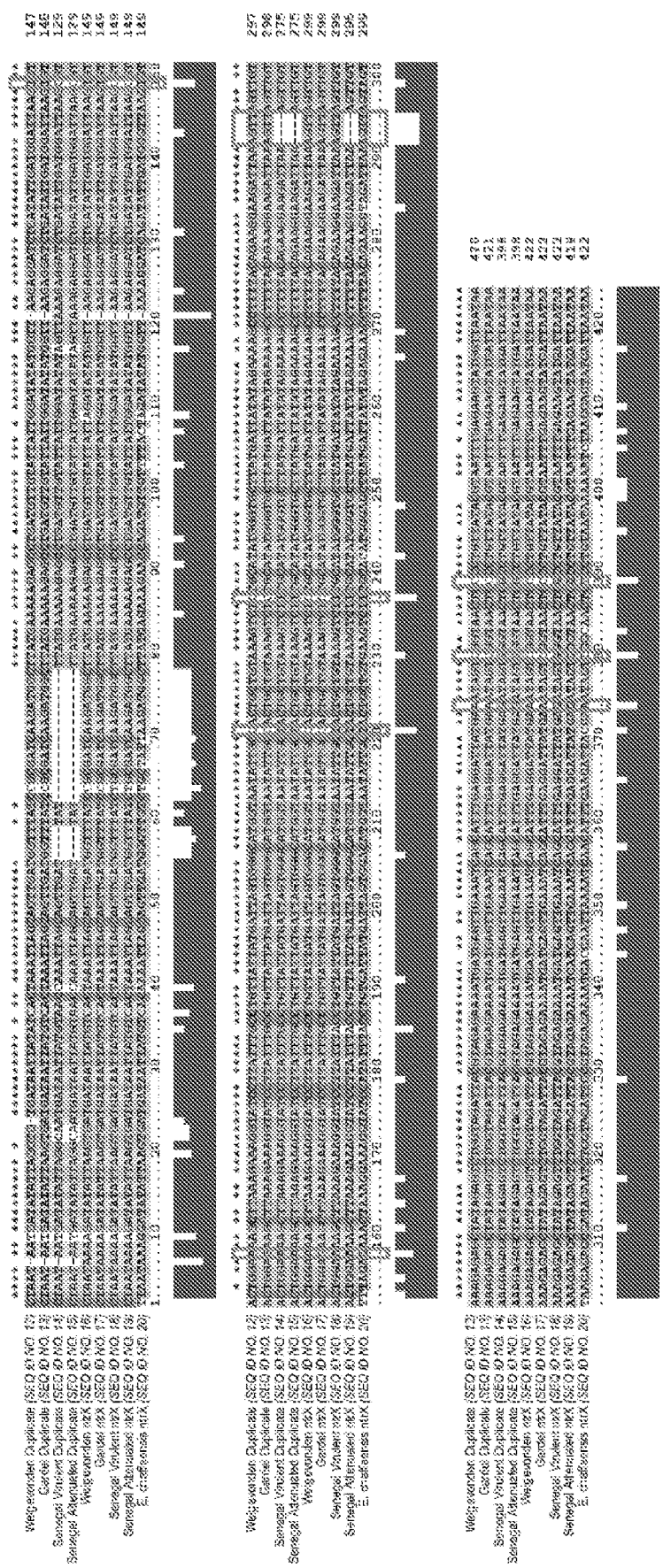

14 Claims, 2 Drawing Sheets
Specification includes a Sequence Listing.

SEQUENCE LISTING

```
<160> NUMBER OF SEQ ID NOS: 22

<210> SEQ ID NO 1
<211> LENGTH: 471
<212> TYPE: PRT
<213> ORGANISM: Ehrlichia ruminantum

<400> SEQUENCE: 1

Met Ala Gln Asp Phe Glu Met Ser Lys Glu Arg Leu Tyr Ile Ser Glu
1               5                   10                  15

Val Leu Val Val Asp Asp Glu Val Asp Ile Arg Asn Leu Ile Lys Asp
            20                  25                  30

Ile Leu Ser Asp Asp Asn Tyr Val Thr Lys Leu Ala Val Asp Gly Leu
        35                  40                  45

Ser Ala Ile Lys Met Ala Tyr Glu Lys Glu Pro Asp Val Val Leu Leu
    50                  55                  60

Asp Ile Trp Leu Arg Gly Ser Asp Ile Asp Gly Leu Ser Val Leu Glu
65                  70                  75                  80

Lys Leu Lys Glu Arg Tyr Pro Tyr Leu Pro Val Ile Met Ile Ser Gly
                85                  90                  95

His Gly Asn Ile Ala Thr Ala Val Lys Ser Leu His Met Gly Ala Tyr
            100                 105                 110

Asp Tyr Ile Glu Lys Pro Phe Thr Glu Gly Arg Leu Lys Leu Val Val
        115                 120                 125

Lys Arg Ala Ile Glu Ser Gly Arg Leu Arg Arg Glu Asn Asp Glu Leu
    130                 135                 140

Lys Ser Ala Phe Glu Asp Tyr Glu Ile Val Gly Asn Ser Pro Val Ile
145                 150                 155                 160

Arg Asn Leu Arg Ser Met Ile Asn Lys Ala Ala Thr Thr Ser Ser Arg
                165                 170                 175

Ile Leu Ile Thr Gly Ser Pro Gly Val Gly Lys Glu Val Val Ala Arg
            180                 185                 190

Leu Ile His Lys Lys Ser Lys Gly Tyr Asp Thr Pro Phe Ile Ser Met
```

```
                195                 200                 205
Tyr Ser Ser Met Leu Pro Ala Asn Asn Tyr Leu Val Asn Ile Phe Gly
    210                 215                 220

Ser Glu Glu Ser Asn Asn Ile Leu Ser His Arg Val Pro His Ile
225                 230                 235                 240

Gly Ile Ile Glu Gln Ala Asn His Gly Thr Leu Phe Ile Asp Glu Val
                245                 250                 255

Thr Asp Leu Arg Tyr Asp Thr Gln Leu Arg Leu Leu Arg Leu Leu Gln
            260                 265                 270

Glu Gly Lys Ile Tyr Arg Glu Asn Ser Lys Ile Pro Val Ser Ile Asp
        275                 280                 285

Val Arg Ile Ile Val Ser Ser Lys Asp Ile Glu Ser Glu Val Lys
    290                 295                 300

Ala Gly Arg Phe Cys Glu Asp Leu Tyr Tyr Arg Leu Asn Val Leu Pro
305                 310                 315                 320

Ile Arg Val Pro Ser Leu Val Glu Tyr Cys Thr Asp Ile Pro Glu Leu
                325                 330                 335

Cys Arg Tyr Phe Met Asn Ser Ile Cys Lys Lys Ile Gly Leu Cys Thr
            340                 345                 350

His Val Leu Ser Asp Glu Ala Leu Ile Ala Met Gln Ser Tyr Glu Trp
        355                 360                 365

Pro Gly Asn Leu Arg Gln Leu Arg Asn Val Ile Glu Trp Ile Leu Ile
    370                 375                 380

Met Lys Ser Pro Lys Glu Met Ile Thr Ala Lys Asp Leu Pro Val Asp
385                 390                 395                 400

Ile Val Ser Asn Ser Pro Ile Asn Asp Val Leu Ser Ala Lys Val Ile
                405                 410                 415

Ser Val Pro Leu Arg Lys Ala Arg Glu Glu Phe Glu Arg Gln Tyr Leu
            420                 425                 430

Lys Thr Gln Leu Ser Arg Phe Gly Gly Asn Val Ser Arg Thr Ala Glu
        435                 440                 445

Phe Val Gly Met Glu Arg Ser Ala Leu His Arg Lys Leu Lys Ile Leu
    450                 455                 460

Gly Leu Cys Asn Val Ser Glu
465                 470

<210> SEQ ID NO 2
<211> LENGTH: 471
<212> TYPE: PRT
<213> ORGANISM: Ehrlichia chaffeensis

<400> SEQUENCE: 2

Met Ala Gln Asn Phe Glu Met Ser Lys Glu Arg Leu Tyr Ile

```
His Gly Asn Ile Ala Thr Ala Val Lys Ser Leu His Met Gly Ala Tyr
                100                 105                 110

Asp Tyr Ile Glu Lys Pro Phe Thr Glu Gly Arg Leu Lys Leu Val Val
            115                 120                 125

Lys Arg Ala Ile Glu Ser Gly Arg Leu Arg Arg Glu Asn Asp Glu Leu
        130                 135                 140

Lys Ser Thr Phe Glu Asp Tyr Glu Ile Val Gly Asn Ser Pro Val Ile
145                 150                 155                 160

Lys Asn Leu Arg Ser Met Ile Asn Lys Ala Thr Thr Ser Ser Arg
                165                 170                 175

Ile Leu Ile Thr Gly Ser Pro Gly Val Gly Lys Glu Val Val Ala Arg
                180                 185                 190

Leu Ile His Lys Lys Ser Lys Gly Tyr Asp Thr Pro Phe Ile Ser Met
            195                 200                 205

Tyr Ser Ser Met Leu Pro Ala Asn Asn Tyr Leu Val Asn Ile Phe Gly
        210                 215                 220

Ser Glu Glu Ser Ser Asn Ile Leu Ser His Arg Val Pro Pro His Ile
225                 230                 235                 240

Gly Ile Ile Glu Gln Ala Asn His Gly Thr Leu Phe Ile Asp Glu Val
                245                 250                 255

Thr Asp Leu Arg Tyr Asp Thr Gln Leu Arg Leu Leu Arg Leu Leu Gln
            260                 265                 270

Glu Gly Lys Ile Tyr Arg Glu Asn Ser Lys Ile Pro Val Ser Val Asp
        275                 280                 285

Val Arg Ile Ile Val Ser Ser Ser Lys Asp Ile Glu Asn Glu Val Arg
290                 295                 300

Ala Gly Lys Phe Cys Glu Asp Leu Tyr Tyr Arg Leu Asn Val Leu Pro
305                 310                 315                 320

Ile Arg Val Pro Ser Leu Val Glu Tyr Cys Thr Asp Ile Pro Glu Leu
                325                 330                 335

Cys Arg Tyr Phe Met Ser Ser Ile Cys Lys Lys Ile Gly Leu Cys Thr
            340                 345                 350

His Ile Leu Ser Asp Glu Ala Leu Ile Ala Met Gln Ser Tyr Glu Trp
        355                 360                 365

Pro Gly Asn Leu Arg Gln Leu Arg Asn Val Ile Glu Trp Ile Leu Ile
370                 375                 380

Met Lys Ser Pro Lys Glu Ile Ile Thr Ala Lys Asp Leu Pro Val Asp
385                 390                 395                 400

Ile Val Ser Asn Ser Pro Ile Asn Asp Val Leu Ser Ala Lys Val Ile
                405                 410                 415

Ser Val Pro Leu Arg Gln Ala Arg Glu Glu Phe Glu Arg Gln Tyr Leu
            420                 425                 430

Lys Thr Gln Leu Ser Arg Phe Gly Gly Asn Val Ser Lys Thr Ala Glu
        435                 440                 445

Phe Val Gly Met Glu Arg Ser Ala Leu His Arg Lys Leu Lys Val Leu
450                 455                 460

Gly Leu Cys Ser Ile Ser Glu
465                 470

<210> SEQ ID NO 3
<211> LENGTH: 471
<212> TYPE: PRT
<213> ORGANISM: Ehrlichia sp. HF

<400> SEQUENCE: 3
```

```
Met Ala Gln Ser Phe Glu Met Ser Lys Glu Arg Leu Tyr Ile Ser Glu
1               5                   10                  15

Val Leu Val Val Asp Asp Glu Val Asp Ile Arg Asn Leu Ile Lys Asp
            20                  25                  30

Ile Leu Ser Asp Asp Asn Tyr Val Thr Lys Leu Ala Val Asp Gly Leu
            35                  40                  45

Ser Ala Ile Lys Met Ala Tyr Glu Lys Glu Pro Asp Val Val Leu Leu
    50                  55                  60

Asp Ile Trp Leu Lys Gly Ser Asp Ile Asp Gly Leu Ser Val Leu Glu
65                      70                  75                  80

Lys Leu Lys Glu Arg Tyr Pro Tyr Leu Pro Val Ile Met Ile Ser Gly
                85                  90                  95

His Gly Asn Ile Ala Thr Ala Val Lys Ser Leu His Met Gly Ala Tyr
                100                 105                 110

Asp Tyr Ile Glu Lys Pro Phe Thr Glu Gly Arg Leu Lys Leu Val Val
            115                 120                 125

Lys Arg Ala Ile Glu Ser Gly Arg Leu Arg Arg Glu Asn Asp Glu Leu
    130                 135                 140

Lys Ser Thr Phe Glu Asp Tyr Glu Ile Val Gly Asn Ser Ser Val Ile
145                 150                 155                 160

Lys Asn Leu Arg Ser Met Ile Asn Lys Ala Ala Thr Thr Ser Ser Arg
                165                 170                 175

Ile Leu Ile Thr Gly Ser Pro Gly Val Gly Lys Glu Val Val Ala Arg
            180                 185                 190

Leu Ile His Lys Lys Ser Lys Gly Tyr Asp Thr Pro Phe Ile Ser Met
            195                 200                 205

Tyr Ser Ser Met Leu Pro Ala Asn Asn Tyr Leu Val Asn Ile Phe Gly
    210                 215                 220

Ser Glu Glu Ser Ser Asn Ile Leu Ser His Arg Val Pro Pro His Ile
225                 230                 235                 240

Gly Ile Ile Glu Gln Ala Asn His Gly Thr Leu Phe Ile Asp Glu Val
            245                 250                 255

Thr Asp Leu Arg Tyr Asp Thr Gln Leu Arg Leu Leu Arg Leu Leu Gln
            260                 265                 270

Glu Gly Lys Ile Tyr Arg Glu Asn Ser Lys Ile Pro Val Ser Val Asp
            275                 280                 285

Val Arg Ile Ile Val Ser Ser Ser Lys Asp Ile Glu Asn Glu Val Lys
    290                 295                 300

Ala Gly Lys Phe Cys Glu Asp Leu Tyr Tyr Arg Leu Asn Val Leu Pro
305                 310                 315                 320

Ile Arg Val Pro Ser Leu Val Glu Tyr Cys Thr Asp Ile Pro Glu Leu
                325                 330                 335

Cys Arg Tyr Phe Met Asn Ser Ile Cys Lys Lys Ile Gly Leu Cys Thr
                340                 345                 350

His Ile Leu Ser Asp Glu Ala Leu Ile Ala Met Gln Ser Tyr Glu Trp
            355                 360                 365

Pro Gly Asn Leu Arg Gln Leu Arg Asn Val Ile Glu Trp Ile Leu Ile
    370                 375                 380

Met Lys Ser Pro Lys Glu Ile Ile Thr Ala Lys Asp Leu Pro Val Asp
385                 390                 395                 400

Ile Val Ser Asn Ser Pro Ile Asn Asp Val Leu Ser Ala Lys Val Ile
                405                 410                 415
```

-continued

```
Ser Ile Pro Leu Arg Gln Ala Arg Glu Phe Glu Lys Gln Tyr Leu
            420                 425                 430

Lys Thr Gln Leu Ser Arg Phe Gly Gly Asn Val Ser Lys Thr Ala Glu
            435                 440                 445

Phe Val Gly Met Glu Arg Ser Ala Leu His Arg Lys Leu Lys Val Leu
450                 455                 460

Gly Leu Cys Asn Met Ser Glu
465                 470

<210> SEQ ID NO 4
<211> LENGTH: 471
<212> TYPE: PRT
<213> ORGANISM: Ehrlichia muris

<400> SEQUENCE: 4

Met Ala Gln Asn Phe Glu Met Ser Lys Glu Arg Leu Tyr Ile Ser Glu
1               5                   10                  15

Val Leu Val Val Asp Asp Glu Val Asp Ile Arg Asn Leu Ile Lys Asp
            20                  25                  30

Ile Leu Ser Asp Asp Asn Tyr Val Thr Lys Leu Ala Val Asp Gly Leu
        35                  40                  45

Ser Ala Ile Lys Met Ala Tyr Glu Lys Glu Pro Asp Val Val Leu Leu
    50                  55                  60

Asp Ile Trp Leu Lys Gly Ser Asp Ile Asp Gly Leu Ser Val Leu Glu
65                  70                  75                  80

Lys Leu Lys Glu Arg Tyr Pro Tyr Leu Pro Val Ile Met Ile Ser Gly
                85                  90                  95

His Gly Asn Ile Ala Thr Ala Val Lys Ser Leu His Met Gly Ala Tyr
            100                 105                 110

Asp Tyr Ile Glu Lys Pro Phe Thr Glu Gly Arg Leu Lys Leu Val Val
        115                 120                 125

Lys Arg Ala Ile Glu Ser Gly Arg Leu Arg Arg Glu Asn Asp Glu Leu
    130                 135                 140

Lys Ser Thr Phe Glu Asp Tyr Glu Ile Val Gly Asn Ser Ser Val Ile
145                 150                 155                 160

Lys Asn Leu Arg Ser Met Ile Asn Lys Ala Ala Thr Thr Ser Ser Arg
                165                 170                 175

Ile Leu Ile Thr Gly Ser Pro Gly Val Gly Lys Glu Val Val Ala Arg
            180                 185                 190

Leu Ile His Lys Lys Ser Lys Gly Tyr Asp Thr Pro Phe Ile Ser Met
        195                 200                 205

Tyr Ser Ser Met Leu Pro Ala Asn Asn Tyr Leu Val Asn Ile Phe Gly
    210                 215                 220

Ser Glu Glu Ser Ser Asn Ile Leu Ser His Arg Val Pro Pro His Ile
225                 230                 235                 240

Gly Ile Ile Glu Gln Ala Asn His Gly Thr Leu Phe Ile Asp Glu Val
                245                 250                 255

Thr Asp Leu Arg Tyr Asp Thr Gln Leu Arg Leu Leu Arg Leu Leu Gln
            260                 265                 270

Glu Gly Lys Ile Tyr Arg Glu Asn Ser Lys Ile Pro Val Gly Val Asp
        275                 280                 285

Val Arg Ile Ile Val Ser Ser Lys Asp Ile Glu Asn Glu Val Lys
    290                 295                 300

Ala Gly Lys Phe Cys Glu Asp Leu Tyr Tyr Arg Leu Asn Val Leu Pro
305                 310                 315                 320
```

```
Ile Arg Val Pro Ser Leu Val Glu Tyr Cys Thr Asp Ile Pro Glu Leu
            325                 330                 335

Cys Arg Tyr Phe Met Asn Ser Ile Cys Lys Lys Ile Gly Leu Cys Thr
            340                 345                 350

Tyr Ile Leu Ser Asp Glu Ala Leu Ile Ala Met Gln Ser Tyr Glu Trp
            355                 360                 365

Pro Gly Asn Leu Arg Gln Leu Arg Asn Val Ile Glu Trp Ile Leu Ile
        370                 375                 380

Met Lys Ser Pro Lys Glu Ile Ile Thr Ala Lys Asp Leu Pro Val Asp
385                 390                 395                 400

Ile Val Ser Asn Ser Pro Ile Asn Asp Val Leu Ser Ala Lys Val Ile
                405                 410                 415

Ser Ile Pro Leu Arg Gln Ala Arg Glu Glu Phe Glu Lys Gln Tyr Leu
            420                 425                 430

Lys Thr Gln Leu Ser Arg Phe Gly Gly Asn Val Ser Lys Thr Ala Glu
            435                 440                 445

Phe Val Gly Met Glu Arg Ser Ala Leu His Arg Lys Leu Lys Val Leu
            450                 455                 460

Gly Leu Cys Asn Ile Ser Glu
465                 470

<210> SEQ ID NO 5
<211> LENGTH: 471
<212> TYPE: PRT
<213> ORGANISM: Ehrlichia canis

<400> SEQUENCE: 5

Met Ala Gln Asp Phe Glu Met Ser Lys Glu Arg Leu Tyr Ile Ser Glu
1               5                   10                  15

Val Leu Val Val Asp Asp Glu Gly Asp Ile Arg Asn Leu Ile Lys Asp
                20                  25                  30

Ile Leu Ser Asp Asp Asn His Gly Thr Lys Leu Ala Val Asp Gly Leu
            35                  40                  45

Ser Ala Ile Lys Met Ala Tyr Glu Lys Glu Pro Asp Val Val Leu Leu
        50                  55                  60

Asp Ile Trp Leu Lys Gly Ser Asp Ile Asp Gly Leu Ser Val Leu Glu
65                  70                  75                  80

Lys Leu Lys Glu Arg Tyr Pro His Leu Pro Val Ile Val Ile Ser Gly
                85                  90                  95

His Gly Asn Ile Ala Thr Ala Val Lys Ser Leu His Ile Gly Ala Tyr
            100                 105                 110

Asp Tyr Ile Glu Lys Pro Phe Thr Glu Ser Arg Leu Lys Leu Val Val
        115                 120                 125

Lys Arg Ala Ile Glu Ser Gly Arg Leu Arg Arg Glu Asn Asp Glu Leu
130                 135                 140

Lys Ser Ala Phe Glu Asp Tyr Glu Ile Val Gly Ser Ser Ser Val Ile
145                 150                 155                 160

Lys Asn Leu Arg Ser Met Val Asn Lys Ala Ala Ala Thr Ser Ser Arg
                165                 170                 175

Ile Leu Ile Thr Gly Ser Pro Gly Val Gly Lys Glu Val Val Ala Arg
            180                 185                 190

Leu Ile His Lys Lys Ser Lys Gly Tyr Asp Thr Pro Phe Ile Ser Met
        195                 200                 205

Tyr Ser Ser Met Leu Pro Ala Asn Asn Tyr Leu Val Asn Ile Phe Gly
```

```
                    210                 215                 220
Ser Glu Glu Ser Ser Asn Ile Leu Ser His Arg Val Pro Pro His Ile
225                 230                 235                 240

Gly Ile Ile Glu Gln Ala Asn Arg Gly Thr Leu Phe Ile Asp Glu Val
                    245                 250                 255

Thr Asp Leu Arg Tyr Asp Thr Gln Leu Arg Leu Leu Arg Leu Leu Gln
                260                 265                 270

Glu Gly Lys Ile Tyr Arg Glu Asn Ser Lys Val Pro Val Ser Val Asp
            275                 280                 285

Val Arg Ile Ile Val Ser Ser Ser Lys Asp Ile Glu Asn Glu Val Arg
        290                 295                 300

Ala Gly Lys Phe Cys Glu Asp Leu Tyr Tyr Arg Leu Asn Val Leu Pro
305                 310                 315                 320

Ile Arg Val Pro Ser Leu Val Glu Tyr Cys Thr Asp Ile Pro Glu Leu
                    325                 330                 335

Cys Arg Tyr Phe Met Asn Ser Ile Cys Lys Lys Met Gly Leu Cys Thr
                340                 345                 350

His Ile Leu Ser Asp Glu Ala Leu Ile Ala Met Gln Ser Tyr Glu Trp
            355                 360                 365

Pro Gly Asn Leu Arg Gln Leu Arg Asn Val Ile Glu Trp Ile Leu Ile
        370                 375                 380

Met Lys Ser Pro Lys Glu Val Ile Thr Ala Lys Asp Leu Pro Val Asp
385                 390                 395                 400

Ile Val Ser Asn Ser Pro Ile Asn Asp Val Leu Ser Ala Lys Val Ile
                    405                 410                 415

Ser Val Pro Leu Arg Gln Ala Arg Glu Glu Phe Glu Arg Gln Tyr Leu
                420                 425                 430

Lys Thr Gln Leu Ser Arg Phe Gly Gly Asn Val Ser Lys Thr Ala Glu
            435                 440                 445

Phe Val Gly Met Glu Arg Ser Ala Leu His Arg Lys Leu Lys Val Leu
        450                 455                 460

Gly Leu Cys Asn Ile Ser Glu
465                 470

<210> SEQ ID NO 6
<211> LENGTH: 471
<212> TYPE: PRT
<213> ORGANISM: Ehrlichia minasensis

<400> SEQUENCE: 6

Met Ala Gln Asp Phe Glu Met Ser Lys Glu Arg Leu Tyr Ile Ser Glu
1               5                   10                  15

Val Leu Val Val Asp Asp Glu Gly Asp Ile Arg Asn Leu Ile Lys Asp
                20                  25                  30

Ile Leu Ser Asp Asp Asn His Gly Thr Lys Leu Ala Val Asp Gly Leu
            35                  40                  45

Ser Ala Ile Lys Met Ala Tyr Glu Lys Glu Pro Asp Val Val Leu Leu
        50                  55                  60

Asp Ile Trp Leu Lys Gly Ser Asp Ile Asp Gly Leu Ser Val Leu Glu
65                  70                  75                  80

Lys Leu Lys Glu Arg Tyr Pro His Leu Pro Val Ile Val Ile Ser Gly
                85                  90                  95

His Gly Asn Ile Ala Thr Ala Val Lys Ser Leu His Ile Gly Ala Tyr
            100                 105                 110
```

```
Asp Tyr Ile Glu Lys Pro Phe Thr Glu Ser Arg Leu Lys Leu Val Val
            115                 120                 125

Lys Arg Ala Ile Glu Ser Gly Arg Leu Arg Glu Asn Asp Glu Leu
130                 135                 140

Lys Ser Ala Phe Glu Asp Tyr Glu Ile Val Gly Ser Ser Val Ile
145                 150                 155                 160

Lys Asn Leu Arg Ser Met Val Asn Lys Ala Ala Thr Ser Ser Arg
                165                 170                 175

Ile Leu Ile Thr Gly Ser Pro Gly Gly Lys Glu Val Val Ala Arg
                180                 185                 190

Leu Ile His Lys Lys Ser Lys Gly Tyr Asp Thr Pro Phe Ile Ser Met
            195                 200                 205

Tyr Ser Ser Met Leu Pro Ala Asn Asn Tyr Leu Val Asn Ile Phe Gly
            210                 215                 220

Ser Glu Glu Ser Ser Asn Ile Leu Ser His Arg Val Pro Pro His Ile
225                 230                 235                 240

Gly Ile Ile Glu Gln Ala Asn Arg Gly Thr Leu Phe Ile Asp Glu Val
                245                 250                 255

Thr Asp Leu Arg Tyr Asp Thr Gln Leu Arg Leu Leu Arg Leu Leu Gln
            260                 265                 270

Glu Gly Lys Ile Tyr Arg Glu Asn Ser Lys Val Pro Val Ser Val Asp
            275                 280                 285

Val Arg Ile Ile Val Ser Ser Ser Lys Asp Ile Glu Asn Glu Val Arg
290                 295                 300

Ala Gly Lys Phe Cys Glu Asp Leu Tyr Tyr Arg Leu Asn Val Leu Pro
305                 310                 315                 320

Ile Arg Val Pro Ser Leu Val Glu Tyr Cys Thr Asp Ile Pro Glu Leu
                325                 330                 335

Cys Arg Tyr Phe Met Asn Ser Ile Cys Lys Lys Met Gly Leu Cys Thr
                340                 345                 350

His Ile Leu Ser Asp Glu Ala Leu Ile Ala Met Gln Ser Tyr Glu Trp
            355                 360                 365

Pro Gly Asn Leu Arg Gln Leu Arg Asn Val Ile Glu Trp Ile Leu Ile
370                 375                 380

Met Lys Ser Pro Lys Glu Ile Ile Thr Ala Lys Asp Leu Pro Val Asp
385                 390                 395                 400

Ile Val Ser Asn Ser Pro Ile Asn Asp Val Leu Ser Ala Lys Val Ile
                405                 410                 415

Ser Val Pro Leu Arg Gln Ala Arg Glu Glu Phe Glu Arg Gln Tyr Leu
            420                 425                 430

Lys Thr Gln Leu Ser Arg Phe Gly Gly Asn Val Ser Lys Thr Ala Glu
            435                 440                 445

Phe Val Gly Met Glu Arg Ser Ala Leu His Arg Lys Leu Lys Val Leu
            450                 455                 460

Gly Leu Cys Asn Ile Ser Glu
465                 470

<210> SEQ ID NO 7
<211> LENGTH: 470
<212> TYPE: PRT
<213> ORGANISM: Candidatus Neoehrlichia lotoris

<400> SEQUENCE: 7

Met Leu Lys Ala Lys Arg Phe Cys Ile Ser Glu Val Leu Ile Val Asp
1               5                   10                  15
```

```
Asp Glu Ala Asp Ile Arg Asn Leu Ile Arg Asp Ile Leu Ser Asp Glu
             20                  25                  30

Asn Tyr Ala Thr Lys Ser Ser Val Asp Gly Leu Ser Ala Ile Lys Leu
         35                  40                  45

Ala Tyr Glu Lys Glu Pro Asp Val Val Leu Leu Asp Ile Trp Leu Lys
 50                  55                  60

Gly Ser Asp Val Asp Gly Leu Ser Val Leu Glu Lys Leu Lys Glu Arg
 65                  70                  75                  80

Tyr Pro Tyr Leu Pro Val Ile Met Ile Ser Gly His Gly Asn Val Ala
                 85                  90                  95

Thr Ala Val Lys Ser Leu His Lys Gly Ala Tyr Asp Tyr Ile Glu Lys
             100                 105                 110

Pro Phe Thr Glu Asn Arg Leu Lys Leu Ala Val Lys Arg Ala Ile Glu
         115                 120                 125

Ser Gly Arg Leu Arg Arg Glu Asn Asp Glu Leu Lys Ala Ser Phe Glu
130                 135                 140

Asp Tyr Glu Phe Ile Gly Asn Ser Pro Val Ile Arg Asn Leu Arg Asn
145                 150                 155                 160

Ile Ile Glu Lys Ala Ser Ile Thr Ser Ser Arg Val Leu Ile Thr Gly
                 165                 170                 175

Ala Ser Gly Thr Gly Lys Glu Val Val Ala Arg Leu Ile His Lys Lys
             180                 185                 190

Ser Lys Gly Cys Asp Thr Pro Phe Val Thr Met Cys Thr Ser Met Met
         195                 200                 205

Pro Ala Asn Asn Tyr Leu Ala Asn Ile Phe Gly Ile Glu Glu Tyr Ser
210                 215                 220

Asn Ser Leu Pro Asn Lys Leu Leu Pro Asn Ile Gly Ile Val Glu Gln
225                 230                 235                 240

Ala Asn Arg Gly Thr Leu Phe Ile Asp Glu Val Thr Glu Val Arg Tyr
                 245                 250                 255

Asp Val Gln Leu Arg Leu Leu Arg Leu Leu Gln Glu Gly Lys Ile Tyr
             260                 265                 270

Arg Glu Asn Gly Lys Ile Pro Ile Gly Ile Asp Ala Arg Val Ile Ala
         275                 280                 285

Ala Ser Ser Arg Val Ile Lys Asp Glu Val Lys Leu Gly Arg Phe Cys
290                 295                 300

Glu Asp Leu Tyr Tyr Arg Leu Asn Val Leu Pro Ile Val Val Pro Ser
305                 310                 315                 320

Leu Cys Glu Tyr Cys Ser Asp Ile Pro Glu Ile Cys Arg Tyr Phe Met
                 325                 330                 335

Lys Ser Ile Cys Lys Lys Met Gly Leu Ala Asp His Val Ile Ser Asn
             340                 345                 350

Asp Ala Ile Ile Ala Met Gln Ser Tyr Ser Trp Pro Gly Asn Leu Arg
         355                 360                 365

Gln Leu Arg Asn Val Leu Glu Trp Val Leu Ile Met Lys Ser Ser Glu
370                 375                 380

Gly Ile Ile Thr Val Glu Asp Leu Pro Ala Glu Ile Ile Ser Gly Ser
385                 390                 395                 400

Ala Val Asn Asp Thr Leu Ser Ala Arg Met Val Ser Val Pro Leu Arg
                 405                 410                 415

Gln Ala Arg Glu Glu Phe Glu Arg Gln Tyr Leu Lys Thr Gln Leu Ser
             420                 425                 430
```

Arg Phe Gly Gly Ser Val Ser Lys Thr Ala Glu Phe Gly Met Glu
            435                 440                 445

Arg Ser Ala Leu His Arg Lys Leu Lys Val Leu Gly Leu Tyr Asn Ile
450                 455                 460

Asp Thr Ala Lys Thr Asn
465                 470

<210> SEQ ID NO 8
<211> LENGTH: 462
<212> TYPE: PRT
<213> ORGANISM: Anaplasma phagocytophilum str. HZ

<400> SEQUENCE: 8

Met Ser Lys Val Lys Arg Phe Tyr Ile Pro Glu Val Leu Ile Val Asp
1               5                   10                  15

Asp Glu Ala Asp Leu Arg Ala Met Ile Gln Asp Ile Leu Arg Asp Asp
            20                  25                  30

Asn Tyr Val Thr Arg Val Ala Ala Asp Gly Leu Ser Ala Met Lys Leu
        35                  40                  45

Ala Tyr Glu Arg Glu Pro Asp Val Val Leu Leu Asp Ile Trp Leu Lys
    50                  55                  60

Gly Ser Asp Ile Asp Gly Leu Ser Val Leu Glu Lys Leu Lys Glu Arg
65                  70                  75                  80

Tyr Pro Ser Leu Pro Val Ile Met Ile Ser Gly His Gly Asn Ile Ala
                85                  90                  95

Thr Ala Val Lys Ser Leu His Ile Gly Ala Tyr Asp Tyr Ile Glu Lys
            100                 105                 110

Pro Phe Thr Glu Asn Arg Leu Lys Leu Val Val Lys Arg Ala Val Glu
        115                 120                 125

Ser Gly Arg Leu Arg Arg Glu Asn Asp Glu Leu Arg Ser Phe Phe Glu
    130                 135                 140

Asp Tyr Glu Leu Ile Gly Asn Ser Pro Gln Ile Lys Ser Leu Arg Ser
145                 150                 155                 160

Thr Val Asn Lys Ala Ala Ser Thr Phe Ser Arg Ile Leu Ile Thr Gly
                165                 170                 175

Ala Pro Gly Thr Gly Lys Glu Val Val Ala Arg Leu Ile His Lys Lys
            180                 185                 190

Phe Arg Gly Gly Ser Thr Phe Val Ser Phe Cys Pro Ser Ile Leu Pro
        195                 200                 205

Glu Asn Ser Tyr Leu Glu Asn Ile Phe Gly Ser Glu Gly Glu Asn Ser
    210                 215                 220

Ser Leu Gln His Val Val Pro His Ser Val Gly Ile Ile Glu Gln Ala
225                 230                 235                 240

Asn His Gly Thr Leu Phe Ile Asp Glu Val Thr Asp Leu Arg Tyr Asp
                245                 250                 255

Ala Gln Leu Arg Leu Met Arg Leu Leu Gln Glu Gly Arg Ile Tyr Arg
            260                 265                 270

Glu Ser Gly Lys Ile Pro Val Ile Val Asp Thr Arg Val Ile Ala Ser
        275                 280                 285

Ser Ser Lys Ile Met Glu Asp Glu Val Arg Leu Gly Lys Phe Cys Glu
    290                 295                 300

Asp Leu Tyr Tyr Arg Leu Asn Val Phe Pro Ile Arg Val Pro Ser Leu
305                 310                 315                 320

Ser Glu Tyr Cys Ala Asp Leu Pro Glu Ile Cys Glu Tyr Met Met Lys
                325                 330                 335

```
Ser Ile Cys Lys Lys Met Arg Leu Phe Pro Arg Ala Ile Ser Glu Glu
            340                 345                 350

Ala Ile Val Ala Met Gln Ser Tyr Cys Trp Pro Gly Asn Leu Arg Gln
            355                 360                 365

Leu Arg Asn Val Leu Glu Trp Val Met Ile Met Gln Thr Lys His Asp
370                 375                 380

Val Ile Thr Val Asp Asp Leu Pro Ala Glu Ile Val Asn Gly Ala Pro
385                 390                 395                 400

Ile Asn Ser Val Phe Thr His Ile Val Ser Ala Pro Leu Arg Lys Ala
            405                 410                 415

Arg Glu Glu Phe Glu Arg Gln Tyr Leu Lys Thr Gln Leu Ser Arg Phe
            420                 425                 430

Gly Gly Ser Val Ser Arg Thr Ala Glu Phe Ile Gly Met Glu Arg Ser
            435                 440                 445

Ala Leu His Arg Lys Leu Lys Met Leu Gly Leu Phe Thr Gly
            450                 455                 460

<210> SEQ ID NO 9
<211> LENGTH: 466
<212> TYPE: PRT
<213> ORGANISM: Anaplasma centrale

<400> SEQUENCE: 9

Met Gly Phe Met Ser Arg Ala Lys Arg Phe Tyr Thr Pro Glu Val Leu
1               5                   10                  15

Ile Val Asp Asp Glu Ala Asp Leu Arg Ala Met Val Gln Asp Ile Leu
            20                  25                  30

Ser Asp Asp Asn Tyr Val Thr Asn Val Ser His Asp Gly Leu Thr Ala
        35                  40                  45

Ile Lys Leu Ala Tyr Glu Arg Glu Pro Asp Val Val Leu Leu Asp Ile
    50                  55                  60

Trp Leu Lys Gly Ser Asp Ile Asp Gly Leu Ser Val Leu Glu Lys Leu
65                  70                  75                  80

Arg Cys Arg Tyr Pro His Leu Pro Val Ile Val Ile Ser Gly His Gly
                85                  90                  95

Asn Ile Ala Thr Ala Val Lys Ser Leu His Ile Gly Ala Tyr Asp Tyr
            100                 105                 110

Ile Glu Lys Pro Phe Thr Glu Asn Arg Leu Lys Leu Val Val Lys Arg
        115                 120                 125

Ala Val Glu Ser Gly Arg Leu Lys Arg Glu Asn Arg Glu Leu Arg Ser
    130                 135                 140

Leu Phe Glu Asp Tyr Glu Ile Val Gly Ser Ser Pro Gln Ile Lys Asn
145                 150                 155                 160

Leu Arg Ser Thr Ile Ser Lys Ala Ala Ser Thr Cys Ser Arg Ile Leu
                165                 170                 175

Ile Thr Gly Ala Pro Gly Thr Gly Lys Glu Val Val Ala Arg Phe Val
            180                 185                 190

His Arg Lys Phe Arg Gly Tyr Asn Ser Ser Phe Val Ser Phe Cys Pro
        195                 200                 205

Ser Ile Leu Pro Glu Ser Ser Tyr Leu Glu Asn Ile Phe Gly Ser Glu
    210                 215                 220

Ser Gly Ser Glu Ala Leu Pro Asn Val Val Pro His Ser Val Gly Ile
225                 230                 235                 240

Ile Glu Gln Ala Asn His Gly Thr Leu Phe Ile Asp Glu Val Thr Asn
```

```
                            245                 250                 255
Leu Arg Tyr Asp Ala Gln Met Arg Leu Met Arg Leu Phe Gln Glu Gly
                260                 265                 270

Arg Ile Tyr Arg Glu His Gly Lys Ser Pro Val Thr Val Asp Thr Arg
            275                 280                 285

Val Ile Ala Ser Ser Arg Ala Ile Glu Glu Val Lys Leu Gly
        290                 295                 300

Arg Phe Cys Glu Asp Leu Tyr Tyr Arg Leu Gly Val Phe Pro Ile Arg
305                 310                 315                 320

Val Pro Ser Leu Ser Glu Tyr Cys Val Asp Leu Pro Glu Val Cys Glu
                325                 330                 335

Tyr Leu Met Arg Ser Ile Cys Arg Lys Met Gly Leu Leu Pro Arg Pro
                340                 345                 350

Ile Ser Glu Asp Ala Ile Ala Met Gln Ser Tyr Ser Trp Pro Gly
                355                 360                 365

Asn Leu Arg Gln Leu Arg Asn Val Leu Glu Trp Ile Leu Ile Met Gln
370                 375                 380

Ser Ser Lys Asp Ile Ile Thr Val Asn Asp Leu Pro Ala Glu Ile Ala
385                 390                 395                 400

Ser Gly Ser Pro Ile Asn Asn Ala Phe Thr Asn Ile Val Ser Ala Pro
                405                 410                 415

Leu Arg Glu Ala Arg Glu Glu Phe Glu Arg His Tyr Leu Arg Thr Gln
                420                 425                 430

Leu Ser Arg Phe Gly Gly Ser Val Ser Lys Thr Ala Glu Phe Ile Lys
                435                 440                 445

Met Glu Arg Ser Ala Leu His Arg Lys Leu Lys Ala Leu Gly Leu Cys
            450                 455                 460

Gly Ser
465

<210> SEQ ID NO 10
<211> LENGTH: 466
<212> TYPE: PRT
<213> ORGANISM: Anaplasma marginale

<400> SEQUENCE: 10

Met Gly Phe Met Ser Arg Ala Lys Arg Phe Tyr Thr Pro Glu Val Leu
1               5                   10                  15

Ile Val Asp Asp Glu Ala Asp Leu Arg Ala Met Val Gln Asp Ile Leu
            20                  25                  30

Ser Asp Asp Asn Tyr Val Thr Lys Ile Ser His Asp Gly Leu Thr Ala
        35                  40                  45

Ile Lys Leu Ala Tyr Glu Arg Glu Pro Asp Val Leu Leu Asp Ile
    50                  55                  60

Trp Leu Lys Gly Ser Asp Ile Asp Gly Leu Ser Val Leu Glu Lys Leu
65                  70                  75                  80

Arg Tyr Arg Tyr Pro His Leu Pro Val Ile Val Ile Ser Gly His Gly
                85                  90                  95

Asn Ile Ala Thr Ala Val Lys Ser Leu His Ile Gly Ala Tyr Asp Tyr
            100                 105                 110

Ile Glu Lys Pro Phe Thr Glu Ser Arg Leu Lys Leu Val Val Lys Arg
        115                 120                 125

Ala Val Glu Ser Gly Arg Leu Lys Arg Glu Asn Tyr Glu Leu Arg Ser
    130                 135                 140
```

```
Leu Phe Glu Asp Tyr Glu Ile Val Gly Ser Ser Pro Gln Ile Lys Asn
145                 150                 155                 160

Leu Arg Ser Thr Ile Ser Lys Ala Ala Ser Thr Cys Ser Arg Ile Leu
            165                 170                 175

Ile Thr Gly Ala Pro Gly Thr Gly Lys Glu Val Val Ala Arg Phe Val
            180                 185                 190

His Arg Lys Phe Lys Gly Cys Asn Ser Ser Phe Val Pro Phe Cys Pro
            195                 200                 205

Ser Ile Leu Pro Glu Ser Ser Tyr Leu Glu Asn Ile Phe Gly Ser Glu
            210                 215                 220

Ser Gly Asn Gly Ala Leu Pro Asn Val Val Pro His Ser Val Gly Ile
225                 230                 235                 240

Ile Glu Gln Ala Asn His Gly Thr Leu Phe Ile Asp Glu Val Thr Asp
                245                 250                 255

Leu Arg Tyr Asp Ala Gln Met Arg Leu Met Arg Leu Leu Gln Glu Gly
            260                 265                 270

Arg Ile Tyr Arg Glu Asn Gly Lys Asn Pro Val Thr Ile Asp Thr Arg
            275                 280                 285

Val Ile Ala Ser Ser Arg Val Ile Glu Glu Val Lys Leu Gly
            290                 295                 300

Arg Phe Cys Glu Asp Leu Tyr Tyr Arg Leu Gly Val Phe Pro Ile Arg
305                 310                 315                 320

Val Pro Ser Leu Ser Glu Tyr Cys Val Asp Ile Pro Glu Val Cys Glu
                325                 330                 335

Tyr Met Met Arg Ser Ile Cys Arg Lys Met Gly Leu Ser Pro Arg Pro
            340                 345                 350

Ile Ser Glu Asp Ala Ile Val Ala Met Gln Ser Tyr Ser Trp Pro Gly
            355                 360                 365

Asn Leu Arg Gln Leu Arg Asn Val Leu Glu Trp Ile Leu Ile Met Gln
            370                 375                 380

Ser Ser Lys Asp Ile Ile Thr Ile Asp Asp Leu Pro Ala Glu Ile Val
385                 390                 395                 400

Ser Gly Ser Pro Ile Asn Asn Val Phe Thr His Ile Val Ser Ala Pro
                405                 410                 415

Leu Arg Lys Ala Arg Glu Glu Phe Glu Arg His Tyr Leu Arg Thr Gln
            420                 425                 430

Leu Ser Arg Phe Gly Gly Ser Val Ser Lys Thr Ala Glu Phe Ile Gly
            435                 440                 445

Met Glu Arg Ser Ala Leu His Arg Lys Leu Lys Ala Leu Gly Leu Cys
450                 455                 460

Gly Ser
465
```

<210> SEQ ID NO 11
<211> LENGTH: 1416
<212> TYPE: DNA
<213> ORGANISM: Ehrlichia ruminantium

<400> SEQUENCE: 11

```
atggcacagg attttgaaat gtccaaggaa agattgtata tttctgaagt attagttgtt      60
gatgatgaag ttgatatcag aaatctaata aaagatatat taagtgatga taattatgtc    120
actaaattag cagttgatgg tttatccgcg atcaagatgg cttatgaaaa agagcctgat    180
gttgtattat tggatatatg gttaagagga tctgatattg atggattaag tgtactggag    240
```

-continued

```
aagcttaaag aaaggtatcc ttatttgcct gttattatga ttagtgggca tggtaatatt      300
gccactgctg taaagtctct gcatatgggt gcttatgatt atatagaaaa gccttttaca      360
gaaggaagat taaagttagt tgtaaagaga gctatagagt ctggtagatt acgtagagaa      420
aatgatgagt tgaaatcagc atttgaggat tatgaaatag tcggtaactc ccctgttata      480
cgtaatttga gaagtatgat taataaagca gctactacat cgagtcgtat actcattact      540
ggttcgccag gtgttggaaa ggaagtagtt gctaggctaa tacataaaaa atccaagggg      600
tatgatactc catttatatc tatgtactca tctatgctac cagctaataa ttacttggtt      660
aatatatttg gtagtgagga agtaataat atattgtctc atagagtacc tcctcatatt      720
ggaattatag agcaagcaaa tcatggtacg ttatttatag atgaagtaac agatttacga      780
tacgatacgc aattaagatt actcagatta ttacaggagg gaaaaatata tagggaaaat      840
agtaagattc ctgttagtat agatgtgaga attattgtgt cttcttccaa agatattgaa      900
agtgaagtaa aagctggtag gttttgtgag gatttatatt atagattaaa tgtccttcca      960
attagagtac cgtctttagt agaatattgt acagatatac cggaattgtg taggtatttt     1020
atgaatagca tctgtaaaaa aataggtttg tgtactcatg tattaagtga tgaagcttta     1080
atagcaatgc agtcatatga atggccaggt aacttaagac aattacgtaa tgttatagaa     1140
tggattttaa ttatgaaatc tcctaaggag atgattacag caaaagattt accagtagat     1200
atagtatcta attcgcctat taatgatgtt ttaagtgcta agttatttc tgtaccatta      1260 cgtaaagctc gtgaagaatt tgaaagacag tatttaaaaa ctcagttatc tcgttttgga     1320
ggtaatgtat cacgaactgc tgaatttgtt ggaatggaac gttcagcatt acaccgtaaa     1380
ttgaaaattc ttggattgtg taatgtttct gaataa                              1416
```

<210> SEQ ID NO 12
<211> LENGTH: 420
<212> TYPE: DNA
<213> ORGANISM: Ehrlichia ruminantum

<400> SEQUENCE: 12

```
ctaataatga tatattaggt gtgataatta tatcactaaa ttagcagttg atggtttatc       60
cgcgatcaag atggcttatg aaaaagagcc tgatgttgta ttattggata tatggttaag     120
aggatctgat attgatggat taagtgtact ggaaaagctt aaagaaaggt atccttattt     180
gcctgttatt atgattagtg ggcatggtaa tattgccact gctgtaaagt ctctgcatat     240
gggtgcttat gattatatag aaaagccttt tacagaagga agattaaagt tagttgtaaa     300
gagagctata gagtctggta gattacgtag agaaaatgat gagttgaaat cagcatttga     360
ggattatgaa atagtcggta actcccctgt tatacgtaat ttgagaagta tggttaataa     420
```

<210> SEQ ID NO 13
<211> LENGTH: 421
<212> TYPE: DNA
<213> ORGANISM: Ehrlichia ruminantum

<400> SEQUENCE: 13

```
ctaataatga tatattaagt gatgataatt atgtcactaa attagcagtt gatggtttat       60
ccgcgatcaa gatggcttat gaaaaagagc tgatgttgt attattggat atatggttaa      120
gaggatctga tattgatgga ttaagtgtac tggagaagct taaagaaagg tatccttatt     180
tgcctgttat tatgattagt gggcatggta atattgccac tgctgtaaag tctctgcata     240
tgggtgctta tgattatata gaaaagcctt ttacagaagg aagattaaag ttagttgtaa     300
```

```
agagagctat agagtctggt agattacgta gagaaaatga tgagttgaaa tcagcatttg    360
aggattatga aatagtcggt aactcccctg ttatacgtaa tttgagaagt atgattaata    420
a                                                                   421
```

<210> SEQ ID NO 14
<211> LENGTH: 398
<212> TYPE: DNA
<213> ORGANISM: Ehrlichia ruminantum

<400> SEQUENCE: 14

```
ctaataatga tatattaggc aatgataatt atgtaaccaa attagcagtt gattatttat     60
gaaaaagagc ctgatgttgt attattggat atatagttaa agaggatctg atattgatgg    120
attaagcgta ctggaaaagc ttaaagaaag gtatccttat ttgcctgtta ttatgattag    180
tgggcatggt aatattgcta ctgctgtaaa gtctttgcat atgggtgctt atgattatat    240
agaaaagcct tttacagaag gaagattaaa gttgtaaaga gagctataga gtctggtaga    300
ttacgtagag aaaatgatga gttgaaatca gcatttgagg attatgagat agtgggtaac    360
tcgcctgtta tacgtaattt gagaagtatg attaataa                            398
```

<210> SEQ ID NO 15
<211> LENGTH: 398
<212> TYPE: DNA
<213> ORGANISM: Ehrlichia ruminantum

<400> SEQUENCE: 15

```
ctaataatga tatattaggc aatgataatt atgtaaccaa attagcagtt gattatttat     60
gaaaaagagc ctgatgttgt attattggat atatagttaa agaggatctg atattgatgg    120
attaagcgta ctggaaaagc ttaaagaaag gtatccttat ttgcctgtta ttatgattag    180
tgggcatggt aatattgcta ctgctgtaaa gtctttgcat atgggtgctt atgattatat    240
agaaaagcct tttacagaag gaagattaaa gttgtaaaga gagctataga gtctggtaga    300
ttacgtagag aaaatgatga gttgaaatca gcatttgagg attatgagat agtgggtaac    360
tcgcctgtta tacgtaattt gagaagtatg attaataa                            398
```

<210> SEQ ID NO 16
<211> LENGTH: 422
<212> TYPE: DNA
<213> ORGANISM: Ehrlichia ruminantum

<400> SEQUENCE: 16

```
ctaataaaag atatattaag tgatgataat tatgtcacta aattagcagt tgatggttta     60
tccgcgatca agatggctta tgaaaaagag cctgatgttg tattattaga tatatggtta    120
agaggatctg atattgatgg attaagtgta ctggaaaagc ttaaagaaag gtatccttat    180
ttgcctgtta ttatgattag tgggcatggt aatattgcca ctgctgtaaa gtctctgcat    240
atgggtgctt atgattatat agaaaagcct tttacagaag gaagattaaa gttagttgta    300
aagagagcta tagagtctgg tagattacgt agagaaaatg atgagttgaa atcagcattt    360
gaggattatg aaatagtcgg taactccccct gttatacgta atttgagaag tatgattaat    420
aa                                                                   422
```

<210> SEQ ID NO 17
<211> LENGTH: 422
<212> TYPE: DNA

<213> ORGANISM: Ehrlichia ruminantum

<400> SEQUENCE: 17

| ctaataaaag atatattaag tgatgataat tatgtcacta aattagcagt tgatggttta | 60 |
| tccgcgatca agatggctta tgaaaaagag cctgatgttg tattattgga tatatggtta | 120 |
| agaggatctg atattgatgg attaagtgta ctggagaagc ttaaagaaag gtatccttat | 180 |
| ttgcctgtta ttatgattag tgggcatggt aatattgcca ctgctgtaaa gtctctgcat | 240 |
| atgggtgctt atgattatat agaaaagcct tttacagaag gaagattaaa gttagttgta | 300 |
| aagagagcta tagagtctgg tagattacgt agagaaaatg atgagttgaa atcagcattt | 360 |
| gaggattatg aaatagtcgg taactcccct gttatacgta atttgagaag tatgattaat | 420 |
| aa | 422 |

<210> SEQ ID NO 18
<211> LENGTH: 422
<212> TYPE: DNA
<213> ORGANISM: Ehrlichia ruminantum

<400> SEQUENCE: 18

| ctaataaaag atatattaag tgatgataat tatgtcacta aattagcagt tgatggttta | 60 |
| tctgcgatca agatggctta tgaaaaagag cctgatgttg tattattgga tatatggtta | 120 |
| agaggatctg atattgatgg attaagcgta ctggaaaagc ttaaagaaag gtatccttat | 180 |
| ttacctgtta ttatgattag tgggcatggt aatattgcta ctgctgtaaa gtctttgcat | 240 |
| atgggtgctt atgattatat agaaaagcct tttacagaag gaagattaaa gttagttgta | 300 |
| aagagagcta tagagtctgg tagattacgt agagaaaatg atgagttgaa atcagcattt | 360 |
| gaggattatg agatagtggg taactcgcct gttatacgta atttgagaag tatgattaat | 420 |
| aa | 422 |

<210> SEQ ID NO 19
<211> LENGTH: 418
<212> TYPE: DNA
<213> ORGANISM: Ehrlichia ruminantum

<400> SEQUENCE: 19

| ctaataaaag atatattaag tgatgataat tatgtcacta aattagcagt tgatggttta | 60 |
| tctgcgatca agatggctta tgaaaaagag cctgatgttg tattattgga tatatggtta | 120 |
| agaggatctg atattgatgg attaagcgta ctggaaaagc ttaaagaaag gtatccttat | 180 |
| ttacctgtta ttatgattag tgggcatggt aatattgcta ctgctgtaaa gtctttgcat | 240 |
| atgggtgctt atgattatat agaaaagcct tttacagaag gaagattaaa gttgtaaaga | 300 |
| gagctataga gtctggtaga ttacgtagag aaaatgatga gttgaaatca gcatttgagg | 360 |
| attatgagat agtgggtaac tcgcctgtta tacgtaattt gagaagtatg attaataa | 418 |

<210> SEQ ID NO 20
<211> LENGTH: 422
<212> TYPE: DNA
<213> ORGANISM: Ehrlichia chaffeensis

<400> SEQUENCE: 20

| ttaataaagg atatattaag tgatgataat tatgtcacaa aattagcagt tgatgggttg | 60 |
| tctgctatta agatggctta tgagaaagaa ccagatgttg ttttactaga tatatggtta | 120 |
| aaaggatcag atattgatgg gttaagtgtt ttagagaaac taaggaaag gtatcccatat | 180 |

```
ttacctgtga ttatgattag tggacatggt aatattgcta ctgctgtgaa gtctttgcac        240
atgggagctt atgattatat agagaaacct tttacagaag gtagattaaa gttagtagtt        300
aagagagcga tagaatctgg tagattgcgt agagaaaatg acgaattaaa atcaacattt        360
gaagattacg aaatagttgg caactctcct gtaataaaaa atctaaggag tatgattaat        420
aa                                                                      422

<210> SEQ ID NO 21
<211> LENGTH: 20
<212> TYPE: DNA
<213> ORGANISM: Artificial Sequence
<220> FEATURE:
<223> OTHER INFORMATION: primer

<400> SEQUENCE: 21
ggaaagattg tatatttctg                                                    20

<210> SEQ ID NO 22
<211> LENGTH: 20
<212> TYPE: DNA
<213> ORGANISM: Artificial Sequence
<220> FEATURE:
<223> OTHER INFORMATION: primer

<400> SEQUENCE: 22
accagtaatg agtatacgac                                                    20
```

LIVE ATTENUATED BACTERIAL STRAIN AND ITS USE AS A VACCINE

FIELD OF THE INVENTION

The present invention relates to a vaccine composition comprising a live attenuated bacterial strain and its use as a vaccine.

BACKGROUND OF THE INVENTION

Vaccines have been one of the biggest success stories of modern medicine. There is arguably no single preventive health intervention more cost-effective than immunization. Time and again, the international community has endorsed the value of vaccines and immunization to prevent and control a large number of infectious diseases and, increasingly, several chronic diseases that are caused by infectious agents.

WHO estimates that at least 10 million human deaths were prevented between 2010 and 2015 thanks to vaccinations delivered around the world. Many millions more lives were protected from the suffering and disability associated with diseases such as pneumonia, diarrhea, whooping cough, measles, and polio.

Thank to vaccination global measles mortality has declined by 79% and the poliomyelitis is closer to be eradicated. Moreover, vaccines can help to limit the spread of antibiotic resistance.

In the last decades, significant advances in the human and veterinary vaccines and their production have been made. One of the main progresses is the improved production efficiency of live attenuated vaccines.

However, there is a still a need for new live attenuated vaccines against human or veterinary pathogens but many obstacles exist that have impeded their development. One of the obstacles to the design of live attenuated vaccine include notably understanding pathogen genetic and antigenic variability, variable host immune responses in order to identify protective antigens, and immunogenicity and identification of the antigens that stimulate protective immunity.

Therefore, it is an object of the invention to overcome at least some of the deficiencies of the existing vaccines and to provide new live attenuated vaccines.

In particular, it is another object of the invention to provide, in at least one embodiment, a live attenuated strain which exhibits an attenuated pathogenicity while maintaining its ability to colonize and which induces a strong protective immunity with limited clinical signs after vaccination and no clinical sign after challenge.

It is also another object of the invention to provide, in at least one embodiment, a method for producing a vaccine which can be adapted to a large number of strains in the same family.

It is also another object of the invention to provide, in at least one embodiment, a method for producing a vaccine which is easy to implement and which is relatively low in production costs.

SUMMARY OF THE INVENTION

Now, the inventors have found that by inactivating or deleting the ntrX gene of a wild bacterial strain they obtain a live strain with an attenuated virulence. Moreover, the inventors have also shown that this live attenuated strain was able to induce immunity sufficient for ensuring protection. Indeed, in order to provide a vaccine, it is not sufficient to provide a live attenuated strain, it is necessary that this strain also induces a strong immune response.

A subject of the present invention is therefore a vaccine composition comprising a bacterial strain with a deleted or inactive ntrX gene.

The present invention also relates to a vaccine composition comprising a bacterial strain with a deleted or inactive ntrX gene for use to induce a protective immune response against the bacterial strain.

The present invention also relates to a vaccine composition comprising a bacterial strain with a deleted or inactive ntrX gene for use as a vaccine.

The present invention also relates to a vaccine composition comprising a bacterial strain with a deleted or inactive ntrX gene for use in preventing an infection caused by the bacterial strain.

In yet another aspect, the present invention relates to method for producing a vaccine composition for use against a bacterial strain comprising a step of:
 inactivating or deleting the ntrX gene of the bacterial strain, thereby obtaining an attenuated bacterial strain.

DETAILED DESCRIPTION OF THE INVENTION

Vaccine Composition

The present invention relates to vaccine composition comprising a bacterial strain with a deleted or inactive ntrX gene. This bacterial strain with a deleted or inactive ntrX gene is a live attenuated strain.

ntrX is transcriptional regulator whose product is Nitrogen assimilation regulatory protein NtrX. It functions as a Signal transduction mechanism (T.COG2204) and contains a "Signal receiver domain; originally thought to be unique to bacteria (CheY, OmpR, NtrC, and PhoB), now recently identified in eukaroytes ETR1 *Arabidopsis thaliana*; this domain receives the signal from the sensor partner in a two-component systems; cd00156".

In one embodiment, the ntrX gene of the invention encodes a NtrX protein having the amino acid sequence of SEQ ID NO: 1.

The NtrX protein having the amino acid sequence of SEQ ID NO: 1 is the NtrX of *Ehrlichia ruminantum* Gardel. The NtrX protein of *Ehrlichia ruminantum* Welgevonden and *Ehrlichia ruminantum* Senegal have also the amino acid sequence of SEQ ID NO: 1.

The amino acid sequence of the NtrX protein of *Ehrlichia ruminantum* Gardel as well as the nucleic acid sequence of the ntrX gene of *Ehrlichia ruminantum* Gardel are given in the Table 1 below.

TABLE 1

| | | |
|---|---|---|
| amino acid sequence of the NtrX protein of *Erlichia ruminantum* Gardel | SEQ ID NO: 1 | MAQDFEMSKERLYISEVLVVDDEVDIRNLI KDILSDDNYVTKLAVDGLSAIKMAYEKEPD VVLLDIWLRGSDIDGLSVLEKLKERYPYLP VIMISGHGNIATAVKSLHMGAYDYIEKPFT EGRLKLVVKRAIESGRLRRENDELKSAFED YEIVGNSPVIRNLRSMINKAATTSSRILIT GSPGVGKEVVARLIHKKSKGYDTPFISMYS SMLPANNYLVNIFGSEESNNILSHRVPPHI GIIEQANHGTLFIDEVTDLRYDTQLRLLRL LQEGKIYRENSKIPVSIDVRIIVSSSKDIE SEVKAGRFCEDLYYRLNVLPIRVPSLVEYC TDIPELCRYFMNSICKKIGLCTHVLSDEAL IAMQSYEWPGNLRQLRNVIEWILIMKSPKE MITAKDLPVDIVSNSPINDVLSAKVISVPL RKAREEFERQYLKTQLSRFGGNVSRTAEFV GMERSALHRKLKILGLCNVSE |

TABLE 1-continued

| nucleic acid sequence of the ntrX gene of Erlichia ruminantum Gardel | SEQ ID NO: 11 | ATGGCACAGGATTTTGAAATGTCCAAGG<br>AAAGATTGTATATTTCTGAAGTATTAGT<br>TGTTGATGATGAAGTTGATATCAGAAAT<br>CTAATAAAAGATATATTAAGTGATGATA<br>ATTATGTCACTAAATTAGCAGTTGATGG<br>TTTATCCGCGATCAAGATGGCTTATGAA<br>AAAGAGCCTGATGTTGTATTATTGGATA<br>TATGGTTAAGAGGATCTGATATTGATGG<br>ATTAAGTGTACTGGAGAAGCTTAAAGAA<br>AGGTATCCTTATTTGCCTGTTATTATGA<br>TTAGTGGGCATGGTAATATTGCCACTGC<br>TGTAAAGTCTCTGCATATGGGTGCTTAT<br>GATTATATAGAAAAGCCTTTTACAGAAG<br>GAAGATTAAAGTTAGTTGTAAAGAGAGC<br>TATAGAGTCTGGTAGATTACGTAGAGAA<br>AATGATGAGTTGAAATCAGCATTTGAGG<br>ATTATGAAATAGTCGGTAACTCCCCTGT<br>TATACGTAATTTGAGAAGTATGATTAAT<br>AAAGCAGCTACTACATCGAGTCGTATAC<br>TCATTACTGGTTCGCCAGGTGTTGGAAA<br>GGAAGTAGTTGCTAGGCTAATACATAAA<br>AAATCCAAGGGGTATGATACTCCATTTA<br>TATCTATGTACTCATCTATGCTACCAGC<br>TAATAATTACTTGGTTAATATATTTGGT<br>AGTGAGGAAAGTAATAATATATTGTCTC<br>ATAGAGTACCTCCTCATATTGGAATTAT<br>AGAGCAAGCAAATCATGGTACGTTATTT<br>ATAGATGAAGTAACAGATTTACGATACG<br>ATACGCAATTAAGATTACTCAGATTATT<br>ACAGGAGGGAAAAATATATAGGGAAAAT<br>AGTAAGATTCCTGTTAGTATAGATGTGA<br>GAATTATTGTGTCTTCTTCCAAAGATAT<br>TGAAAGTGAAGTAAAAGCTGGTAGGTTT<br>TGTGAGGATTTATATTATAGATTAAATG<br>TCCTTCCAATTAGAGTACCGTCTTTAGT<br>AGAATATTGTACAGATATACCGGAATTG<br>TGTAGGTATTTTATGAATAGCATCTGTA<br>AAAAAATAGGTTTGTGTACTCATGTATT<br>AAGTGATGAAGCTTTAATAGCAATGCAG<br>TCATATGAATGGCCAGGTAACTTAAGAC<br>AATTACGTAATGTTATAGAATGGATTTT<br>AATTATGAAATCTCCTAAGGAGATGATT<br>ACAGCAAAAGATTTACCAGTAGATATAG<br>TATCTAATTCGCCTATTAATGATGTTTT<br>AAGTGCTAAAGTTATTTCTGTACCATTA<br>CGTAAAGCTCGTGAAGAATTTGAAAGAC<br>AGTATTTAAAAACTCAGTTATCTCGTTT<br>TGGAGGTAATGTATCACGAACTGCTGAA<br>TTTGTTGGAATGGAACGTTCAGCATTAC<br>ACCGTAAATTGAAAATTCTTGGATTGTG<br>TAATGTTTCTGAATAA |

In another embodiment, the ntrX gene of the invention is an active homologue of the ntrX gene which encodes a NtrX protein having the amino acid sequence of SEQ ID NO: 1; said active homologue encodes a NtrX protein having an amino acid sequence with at least 50% of identity with SEQ ID NO: 1.

Preferably, said active homologue encodes a NtrX protein having an amino acid sequence with at least 60%, more preferably at least 70%, more preferably at least 75%, more preferably at least 80%, more preferably at least 85%, even more preferably at least 90%, and most preferably at least 95% of identity with SEQ ID NO: 1.

For the purposes of comparing two closely-related polynucleotide or polypeptide sequences, the "% identity" between a first sequence and a second sequence may be calculated using an alignment program, such as BLAST® (available at blast.ncbi.nlm.nih.gov) using standard settings. The % identity is the number of identical residues divided by the number of residues in the reference sequence, multiplied by 100. The % identity in the above table is calculated by this methodology.

Alternatively, the % identity may also be calculated by dividing the number of identical residues by the number of aligned residues and multiplying by 100.

Alternative methods include using a gapped method in which gaps in the alignment, for example deletions in one sequence relative to the other sequence, are accounted for in a gap score or a gap cost in the scoring parameter (for more information, see the website blast.ncbi.nlm.nih.gov).

In an embodiment, the inactive ntrX gene is an inactive mutant of a ntrX gene encoding a NtrX protein having the amino acid sequence of SEQ ID NO: 1 or of an active homologue thereof encoding a NtrX protein having an amino acid sequence with at least 50%, 60%, 70%, 75%, 80%, 85%, 90% or 95% of identity with SEQ ID NO: 1. In another embodiment, it is a ntrX gene encoding a NtrX protein having the amino acid sequence of SEQ ID NO: 1 or an active homologue thereof encoding a NtrX protein having an amino acid sequence with at least 50%, 60%, 70%, 75%, 80%, 85%, 90% or 95% of identity with SEQ ID NO: 1 which is deleted.

Preferably, the bacterial strain is genetically engineered so as to delete or to inactivate the ntrX gene.

Advantageously, only the ntrX gene is inactivated or deleted.

In one embodiment, the vaccine composition comprises a bacterial strain with a deleted ntrX gene.

In this embodiment, the bacterial strain is a mutant strain from a bacterial strain, preferably a wild and/or pathogen strain, wherein the ntrX gene has been deleted. The deletion of a gene can be carried out by any methods known by the skilled person. In one embodiment, the ntrX gene which is a ntrX gene encoding a NtrX protein having the amino acid sequence of SEQ ID NO: 1 is deleted.

In another embodiment, the ntrX gene which is an active homologue thereof encoding a NtrX protein having an amino acid sequence with at least 50%, 60%, 70%, 75%, 80%, 85%, 90% or 95% of identity with SEQ ID NO: 1 is deleted.

In another embodiment, the vaccine composition comprises a bacterial strain with an inactive ntrX gene. An inactive ntrX gene may be a ntrX gene which encodes a non-functional NtrX protein or no NtrX protein at all.

In this embodiment, the bacterial strain is a mutant strain from a bacterial strain, preferably a wild and/or pathogen strain, wherein the ntrX gene has been inactivated.

The inactivation of a gene can be carried out by any methods known by the skilled person.

By way of example, inactivation of said ntrX gene can be obtained by mutagenesis and selection of the mutants having lost the NtrX protein activity. Mutagenesis can be performed for instance by targeted deletion of a portion of ntrX coding sequence or by targeted insertion of an exogenous sequence within said coding sequence. Mutagenesis may be also a deletion, an insertion or a replacement of at least one nucleic acid. For example, the inactive mutant of a ntrX gene may be a ntrX gene wherein a codon stop is inserted or wherein a region is deleted and/or rearranged. The inactive mutant of a ntrX gene may also be a ntrX gene wherein at least one nucleic acid has been inserted, for example an inactivating point mutation or an insertion leading to a frameshift mutation.

The inactivation can also be performed by random chemical or physical mutagenesis, followed by screening of the mutants within the ntrX gene. Methods for high throughput mutagenesis and screening are available in the art.

Preferably, a strain with an inactive ntrX gene is a strain wherein the ntrX gene is not expressed.

In one embodiment, the inactive ntrX gene is an inactive mutant of a ntrX gene encoding a NtrX protein having the amino acid sequence of SEQ ID NO: 1.

In another embodiment, the inactive ntrX gene is an inactive mutant of an active homologue of a ntrX gene encoding a NtrX protein having the amino acid sequence of SEQ ID NO: 1; said active homologue encodes a NtrX protein having an amino acid sequence with at least 50% of identity with SEQ ID NO: 1.

Preferably, said active homologue of a ntrX gene encoding a NtrX protein having the amino acid sequence of SEQ ID NO: 1 encodes a NtrX protein having an amino acid sequence with at least 60%, at least 70%, more preferably at least 75%, more preferably at least 80%, more preferably at least 85%, even more preferably at least 90%, and most preferably at least 95% sequence identity with SEQ ID NO: 1.

In one embodiment, the bacterial strain with a deleted or an inactive a ntrX gene is an Alphaproteobacteria strain, preferably a Rickettsiales strain, more preferably an Anaplasmataceae strain.

Anaplasmataceae are genetically related small Gram-negative pleomorphic cocci.

Anaplasmataceae comprises the strains of genus selected from the group consisting of *Anaplasma, Ehrlichia, Neohckettsia,* and *Wolbachia*. Anaplasmataceae are obligatory intracellular bacteria which are mainly transmitted by arthropods, most frequently ticks, lice and mites, and cause major illnesses such as ehrlichiosis and anaplasmosis.

Vaccines directed against strains of Anaplasmataceae remain limited. In particular, only a few cases of live attenuated vaccine directed against Anaplasmataceae have been reported and the possible mechanism of attenuation of such strains has been studied in only a few cases.

For example, in an attempt to produce live attenuated vaccines against *Ehrlichia ruminantium*, a tick-borne intracellular pathogen of ruminants that causes headwater, 3 attenuated strains from Guadeloupe (Gardel), South Africa (Welgevonden) and Senegal have been generated in vitro by passaging the virulent bacterium in bovine endothelial cells, in addition to canine macrophage-monocyte cells for Welgevonden strain (Jongejan 1991; Zweygarth et al. 2005; Pilet et al. 2012; Marcelino et al. 2015).

However, usage of these attenuated strains as vaccines has remained limited due to constraints associated with storage (no cold chain disruption) and intravenous administration. Their mechanisms of attenuation are unknown which is problematic considering the risk of virulence recovery. Moreover, attenuated vaccines, as for any other vaccine against headwater, protect against homologous challenges but confer limited protections against heterologous strains and co-occurrence of different strains in infected animals is common (Zweygadh et al. 2005; Frutos et al. 2006).

Thus, it is also an object of the invention to provide, in at least one embodiment, a vaccine against disease caused by Anaplasmataceae and in particular against ehrlichiosis.

In particular, it is an object of the invention to overcome at least some of the deficiencies of the existing therapies and prophylaxis of disease caused by Anaplasmataceae.

In order to overcome the drawbacks of the prior ad vaccines against Anaplasmataceae, the present invention provides a vaccine composition comprising an Anaplasmataceae strain with a deleted or an inactive ntrX gene.

As shown in the table 2 below, the NtrX protein is highly conserved among the Anaplasmataceae family from 84% to 93% of identity.

TABLE 2

% of identity of NtrX protein between different strains of *Anaplasmataceae*

| Anaplasmataceae strain | Disease caused by the strain | SEQ ID NO of the NtrX protein | Amino acid sequence of NtrX | % of identity with SEQ ID NO: 1 |
|---|---|---|---|---|
| *Ehrlichia ruminantium* Gardel | ehrlichiosis | SEQ ID NO: 1 | MAQDFEMSKERLYISEVLVVDDEVDIRNLIKDILSDDNYVTKLAVDGLSAIKMAY EKEPDVVLLDIWLRGSDIDGLSVLEKLKERYPYLPVIMISGHGNIATAVKSLHMG AYDYIEKPFTEGRLKLVVKRAIESGRLRRENDELKSAFEDYEIVGNSPVIRNLRS MINKAATTSSRILITGSPGVGKEVVARLIHKKSKGYDTPFISMYSSMLPANNYLV NIFGSEESNNILSHRVPPHIGIIEQANHGTLFIDEVTDLRYDTQLRLLRLLQEGK IYRENSKIPVSIDVRIIVSSSKDIESEVKAGRFCEDLYYRLNVLPIRVPSLVEYC TDIPELCRYFMNSICKKIGLCTHVLSDEALIAMQSYEWPGNLRQLRNVIEWILIM KSPKEMITAKDLPVDIVSNSPINDVLSAKVISVPLRKAREEFERQYLKTQLSRFG GNVSRTAEFVGMERSALHRKLKILGLCNVSE | 100% |
| *Ehrlichia chaffeensis* | ehrlichiosis | SEQ ID NO: 2 | MAQNFEMSKERLYISEVLVVDDEVDIRNLIKDILSDDNYVTKLAVDGLSAIKMAY EKEPDVVLLDIWLKGSDIDGLSVLEKLKERYPYLPVIMISGHGNIATAVKSLHMG AYDYIEKPFTEGRLKLVVKRAIESGRLRRENDELKSTFEDYEIVGNSPVIKNLRS MINKAATTSSRILITGSPGVGKEVVARLIHKKSKGYDTPFISMYSSMLPANNYLV NIFGSEESSNILSHRVPPHIGIIEQANHGTLFIDEVTDLRYDTQLRLLRLLQEGK IYRENSKIPVSVDVRIIVSSSKDIENEVRAGKFCEDLYYRLNVLPIRVPSLVEYC TDIPELCRYFMSSICKKIGLCTHILSDEALIAMQSYEWPGNLRQLRNVIEWILIM KSPKEIITAKDLPVDIVSNSPINDVLSAKVISVPLRQAREEFERQYLKTQLSRFG GNVSKTAEFVGMERSALHRKLKVLGLCSISE | 96% |
| *Ehrlichia* sp. HF | ehrlichiosis | SEQ ID NO: 3 | MAQSFEMSKERLYISEVLVVDDEVDIRNLIKDILSDDNYVTKLAVDGLSAIKMAY EKEPDVVLLDIWLKGSDIDGLSVLEKLKERYPYLPVIMISGHGNIATAVKSLHMG AYDYIEKPFTEGRLKLVVKRAIESGRLRRENDELKSTFEDYEIVGNSSVIKNLRS MINKAATTSSRILITGSPGVGKEVVARLIHKKSKGYDTPFISMYSSMLPANNYLV NIFGSEESSNILSHRVPPHIGIIEQANHGTLFIDEVTDLRYDTQLRLLRLLQEGK IYRENSKIPVSVDVRIISSSKDIENEVKAGKFCEDLYYRLNVLPIRVPSLVEYC TDIPELCRYFMNSICKKIGLCTHILSDEALIAMQSYEWPGNLRQLRNVIEWILIM KSPKEIITAKDLPVDIVSNSPINDVLSAKVISIPLRQAREEFEKQYLKTQLSRFG GNVSKTAEFVGMERSALHRKLKVLGLCNMSE | 96% |

TABLE 2-continued

% of identity of NtrX protein between different strains of Anaplasmataceae

| Anaplasmataceae strain | Disease caused by the strain | SEQ ID NO of the NtrX protein | Amino acid sequence of NtrX | % of identity with SEQ ID NO: 1 |
|---|---|---|---|---|
| Ehrlichia muris | ehrlichiosis | SEQ ID NO: 4 | MAQNFEMSKERLYISEVLVVDDEVDIRNLIKDILSDDNYVTKLAVDGLSAIKMAY EKEPDVVLLDIWLKGSDIDGLSVLEKLKERYPYLPVIMISGHGNIATAVKSLHMG AYDYIEKPFTEGRLKLVVKRAIESGRLRRENDELKSTFEDYEIVGNSSVIKNLRS MINKAATTSSRILITGSPGVGKEVVARLIHKKSKGYDTPFISMYSSMLPANNYLV NIFGSEESSNILSHRVPPHIGIIEQANHGTLFIDEVTDLRYDTQLRLLRLLQEGK IYRENSKIPVGVDVRIIVSSSKDIENEVKAGKFCEDLYYRLNVLPIRVPSLVEYC TDIPELCRYFMNSICKKIGLCTYILSDEALIAMQSYEWPGNLRQLRNVIEWILIM KSPKEIITAKDLPVDIVSNSPINDVLSAKVISIPLRQAREEFEKQYLKTQLSRFG GNVSKTAEFVGMERSALHRKLKVLGLCNISE | 96% |
| Ehrlichia canis | ehrlichiosis | SEQ ID NO: 5 | MAQDFEMSKERLYISEVLVVDDEGDIRNLIKDILSDDNHGTKLAVDGLSAIKMA YEKEPDVVLLDIWLKGSDIDGLSVLEKLKERYPHLPVIVISGHGNIATAVKSLHI GAYDYIEKPFTESRLKLVVKRAIESGRLRRENDELKSAFEDYEIVGSSSVIKNLR SMVNKAAATSSRILITGSPGVGKEVVARLIHKKSKGYDTPFISMYSSMLPANNYL VNIFGSEESSNILSHRVPPHIGIIEQANRGTLFIDEVTDLRYDTQLRLLRLLQEG KIYRENSKVPVSVDVRIIVSSSKDIENEVRAGKFCEDLYYRLNVLPIRVPSLVEY CTDIPELCRYFMNSICKKMGLCTHILSDEALIAMQSYEWPGNLRQLRNVIEWILI MKSPKEVITAKDLPVDIVSNSPINDVLSAKVISVPLRQAREEFERQYLKTQLSRF GGNVSKTAEFVGMERSALHRKLKVLGLCNISE | 94% |
| Ehrlichia minasensis | ehrlichiosis | SEQ ID NO: 6 | MAQDFEMSKERLYISEVLVVDDEGDIRNLIKDILSDDNHGTKLAVDGLSAIKMAY EKEPDVVLLDIWLKGSDIDGLSVLEKLKERYPHLPVIVISGHGNIATAVKSLHIG AYDYIEKPFTESRLKLVVKRAIESGRLRRENDELKSAFEDYEIVGSSSVIKNLRS MVNKAAATSSRILITGSPGVGKEVVARLIHKKSKGYDTPFISMYSSMLPANNYLV NIFGSEESSNILSHRVPPHIGIIEQANRGTLFIDEVTDLRYDTQLRLLRLLQEGK IYRENSKVPVSVDVRIIVSSSKDIENEVRAGKFCEDLYYRLNVLPIRVPSLVEYC TDIPELCRYFMNSICKKMGLCTHILSDEALIAMQSYEWPGNLRQLRNVIEWILIM KSPKEIITAKDLPVDIVSNSPINDVLSAKVISVPLRQAREEFERQYLKTQLSRFG GNVSKTAEFVGMERSALHRKLKVLGLCNISE | 94% |
| candidatus Neoehrlichia lotoris | ehrlichiosis | SEQ ID NO: 7 | MLKAKRFCISEVLIVDDEADIRNLIRDILSDENYATKSSVDGLSAIKLAYEKEPD VVLLDIWLKGSDVDGLSVLEKLKERYPYLPVIMISGHGNVATAVKSLHKGAYDYI EKPFTENRLKLAVKRAIESGRLRRENDELKASFEDYEFIGNSPVIRNLRNIIEKA SITSSRVLITGASGTGKEVVARLIHKKSKGCDTPFVTMCTSMMPANNYLANIFGI EEYSNSLPNKLLPNIGIVEQANRGTLFIDEVTEVRYDVQLRLLRLLQEGKIYREN GKIPIGIDARVIAASSRVIKDEVKLGRFCEDLYYRLNVLPIVVPSLCEYCSDIPE ICRYFMKSICKKMGLADHVISNDAIIAMQSYSWPGNLRQLRNVLEWVLIMKSSEG IITVEDLPAEIISGSAVNDTLSARMVSVPLRQAREEFERQYLKTQLSRFGGSVSK TAEFVGMERSALHRKLKVLGLYNIDTAKTN | 78% |
| Anaplasma phagocytophilum | anaplasmosis | SEQ ID NO: 8 | MSKVKRFYIPEVLIVDDEADLRAMIQDILRDDNYVTRVAADGLSAMKLAYEREP DVVLLDIWLKGSDIDGLSVLEKLKERYPSLPVIMISGHGNIATAVKSLHIGAYDY IEKPFTENRLKLVVKRAVESGRLRRENDELRSFFEDYELIGNSPQIKSLRSTVNK AASTFSRILITGAPGTGKEVVARLIHKKSKGSTFVSFCPSILPENSYLENIFGS EGENSSLQHVVPHSVGIIEQANHGTLFIDEVTDLRYDAQLRLMRLLQEGRIYRES GKIPVIVDTRVIASSSKIMEDEVRLGKFCEDLYYRLNVFPIRVPSLSEYCADLPE ICEYMMKSICKKMRLFPRAISEEAIVAMQSYCWPGNLRQLRNVLEWVMIMQTKH DVITVDDLPAEIVNGAPINSVFTHIVSAPLRKAREEFERQYLKTQLSRFGGSVSR TAEFIGMERSALHRKLKMLGLFTG | 74% |
| Anaplasma centrale | anaplasmosis | SEQ ID NO: 9 | MGFMSRAKRFYTPEVLIVDDEADLRAMVQDILSDDNYVTNVSHDGLTAIKLAYE REPDVVLLDIWLKGSDIDGLSVLEKLRCRYPHLPVIVISGHGNIATAVKSLHIGA YDYIEKPFTENRLKLVVKRAVESGRLKRENRELRSLFEDYEIVGSSPQIKNLRST ISKAASTCSRILITGAPGTGKEVVARFVHRKFRGYNSSFVSFCPSI LPESSYLENIFGSESGSEALPNVVPHSVGIIEQANHGTLFIDEVTNLRYDAQMRL MRLFQEGRIYREHGKSPVTVDTRVIASSSRAIEEEVKLGRFCEDLYYRLGVFPIR VPSLSEYCVDLPEVCEYLMRSICRKMGLLPRPISEDAIVAMQSYSWPGNLRQL RNVLEWILIMQSSKDIITVNDLPAEIASGSPINNAFTNIVSAPLREAREEFERHY LRTQLSRFGGSVSKTAEFIKMERSALHRKLKALGLCGS | 72% |
| Anaplasma marginale | anaplasmosis | SEQ ID NO: 10 | MGFMSRAKRFYTPEVLIVDDEADLRAMVQDILSDDNYVTKISHDGLTAIKLAYE REPDVVLLDIWLKGSDIDGLSVLEKLRYRYPHLPVIVISGHGNIATAVKSLHIGA YDYIEKPFTESRLKLVVKRAVESGRLKRENYELRSLFEDYEIVGSSPQIKNLRST ISKAASTCSRILITGAPGTGKEVVARFVHRKFKGCNSSFVPFCPSILPESSYLEN IFGSESGNGALPNVVPHSVGIIEQANHGTLFIDEVTDLRYDAQMRLMRLLQEGRI YRENGKNPVTIDTRVIASSSRVIEEEVKLGRFCEDLYYRLGVFPIRVPSLSEYCV DIPEVCEYMMRSICRKMGLSPRPISEDAIVAMQSYSWPGNLRQLRNVLEWILIMQ SSKDIITIDDLPAEIVSGSPINNVFTHIVSAPLRKAREEFERHYLRTQLSRFGGS VSKTAEFIGMERSALHRKLKALGLCGS | 72% |

Thus, the inactive ntrX gene may be an inactive mutant of a ntrX gene encoding a NtrX protein having the amino acid sequence selected from the group consisting of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9 and SEQ ID NO:10.

In one embodiment, the inactive ntrX gene may be an inactive mutant of a ntrX gene encoding a NtrX protein having at least 50%, 60%, 65%, 70%, 75%, 80%, 85% 90% or 95% of the amino acid sequence selected from the group consisting of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9 and SEQ ID NO:10.

In another embodiment wherein the ntrX gene is deleted, it is a ntrX gene encoding a NtrX protein having the amino acid sequence selected from the group consisting of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9 and SEQ ID NO:10 which is deleted.

In one embodiment, the deleted ntrX gene may be a ntrX gene encoding a NtrX protein having at least 50%, 60%, 65%, 70%, 75%, 80%, 85% 90% or 95% of the amino acid sequence selected from the group consisting of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9 and SEQ ID NO:10.

In a preferred embodiment, the bacterial strain is selected from the group consisting of *Anaplasma* strain, *Ehrlichia* strain, *Wolbachia* strain and Neohckettsia strain.

In a preferred embodiment, the bacterial strain is an *Ehrlichia* strain.

The *Ehrlichia* strain may be selected from the group consisting of *E. canis, E. chaffeensis, E. ewingii, E. muris,* and *E. ruminantium.*

Among the species of the genus *Ehrlichia*, some are species pathogenic for humans and animals such as *E. chaffeensis*, responsible for Human monocytic ehrlichiosis or *E. canis*, the causing agent of canine monocytic ehrlichiosis.

*Ehrlichia ruminantium*, is also pathogenic. This tick-borne intracellular pathogen of ruminants causes heartwater. Heartwater is an economically important tropical disease of ruminants. It can cause up to 80% mortality in susceptible animals. This disease is present in Sub-saharan Africa, islands in the Indian Ocean and the Caribbean, and is threatening the American mainland. It is listed within the 12$^{th}$ most important transboundary animal diseases for US homeland security department.

Preferably, the *Ehrlichia* strain is an *E. ruminantium* strain.

*E. ruminantium* strain may be selected from the group consisting of Senegal, Gardel and Welgevonden *E. ruminantium* strains.

Preferably, the *E. ruminantium* strain is a Senegal *E. ruminantium* strain.

In one embodiment, the vaccine composition comprises a bacterial strain which is not an *E. ruminantium* strain.

In one embodiment, the vaccine composition comprises a bacterial strain which is not a Senegal *E. ruminantium* strain.

In one embodiment, the vaccine composition comprises a bacterial strain which is not an *E. canis* strain.

In one embodiment, the vaccine composition comprises a bacterial strain which is not a *E. canis* Israel strain.

In another embodiment, the bacterial strain is not an Anaplasmataceae strain.

The bacterial strain may also be selected from the group consisting of a *Rickettsia* strain, an *Orientia* strain, a *Bartonella* strain and a *Brucella* strain.

Typically, the vaccine composition may comprise a pharmaceutically acceptable excipient.

If desired, the vaccine composition according to the invention may also comprise an adjuvant. Examples of suitable compounds and compositions with adjuvant activity are well known in the art. Adjuvant may be for example selected from the group consisting of: inorganic adjuvants, organic adjuvants, oil-based adjuvants, cytokines, particulate adjuvants, liposomes, virosomes, bacterial adjuvants, synthetic adjuvants, synthetic polynucleotides adjuvants, immunostimulatory oligonucleotides containing unmethylated CpG dinucleotides and a combination thereof.

In addition to the live attenuated bacterial strain, the vaccine composition can also comprise one or more additional active immunizing agent in order to produce a vaccine composition capable of inducing immunity against a number of different pathogens. The vaccine composition may comprise several live attenuated bacterial strains.

Method of Treatment

The present invention also relates to a vaccine composition according to the invention for use to induce an immune response against a bacterial strain, in particular an Anaplasmataceae strain.

As discussed above, the inventors have found that by inactivating the ntrX gene in a wild bacterial strain they obtain a live strain with an attenuated virulence which induces a protective immune response against the wild bacterial strain in the subject in which it is administered.

As used herein, "subject" refers to a human or animal that may benefit from the administration of a vaccine composition as recited herein.

The subject may be a human or a non-human animal. For example, the non-human animal is selected from the group consisting of a bovine, an ovine, an equine, a feline, a caprine or a canine.

The present invention also relates to a method for inducing an immune response against a bacterial strain, preferably an Anaplasmataceae strain, in a subject in need thereof comprising administering to said subject an effective amount of the vaccine composition of the invention.

The present invention also relates to a vaccine composition according to the invention for use as a vaccine, preferably a prophylaxis vaccine.

The inventors have shown that administering to a subject a vaccine composition comprising bacterial strain attenuated by the inactivation or the deletion of the ntrX gene prevents or alleviates the effects of an infection caused by the wild bacterial strain.

Also provided, a method for protecting or treating a subject against disease caused by a bacterial strain comprising administering to said subject a bacterial strain with a deleted or inactive ntrX gene.

In a preferred embodiment, the vaccine composition is for use in preventing and/or treating an infection caused by bacterial strain, preferably an Anaplasmataceae strain.

The infection caused by an Anaplasmataceae strain is preferably ehrlichiosis or anaplasmosis, more preferably ehrlichiosis.

In order to prevent and/or treat an infection caused by a given wild bacterial strain, it would be preferred to use a vaccine composition comprising the given bacterial strain which has been attenuated by deleting or inactivating its ntrX gene thereby providing an attenuated mutant strain of the given bacterial. For example, for preventing or treating ehrlichiosis, it would be preferred to use an *Ehrlichia* strain with a deleted or an inactive ntrX gene. In the same way, for preventing or treating ehrlichiosis caused by a Senegal *Ehrlichia* strain, it would be preferred to use a Senegal *Ehrlichia* strain with a deleted or an inactive ntrX gene.

In another embodiment, a vaccine composition comprising a bacterial strain from the same genus or species of a given bacterial strain with a deleted or inactive ntrX gene could be used in order to prevent and/or treat an infection caused by the given bacterial strain.

In yet another aspect, the present invention relates to a method for preventing and/or treating a subject in need thereof against an infection caused by a bacterial strain comprising administering to said subject an effective amount of the vaccine composition of the invention.

The vaccine composition may be administered by intramuscular, intradermal, subcutaneous or intranasal inoculation or injection. The vaccine composition is administered in an amount, which is effective to protect the subject against challenge, by a virulent bacterial strain. This amount may vary according to the subject being inoculated, taking into consideration the size and weight of the subject. The vaccine composition according to the invention comprises preferably an effective dosage of the live attenuated bacterial strain as the active component, i.e. a sufficient amount of the bacterial live attenuated strain that will induce immunity in the vaccinated subjects, against challenge by the corresponding virulent bacterial strain.

Method for Producing a Vaccine Composition

In yet another aspect, the present invention provides the use of a bacterial strain, preferably an Anaplasmataceae strain, with a deleted or inactive ntrX gene for the manufacture of a vaccine.

The present invention also relates to a method for producing a vaccine composition for use as a vaccine against a bacterial strain comprising a step of:

inactivating or deleting the ntrX gene of the bacterial strain, thereby obtaining an attenuated bacterial strain.

Preferably, the bacterial strain is an Anaplasmataceae strain.

Examples of Anaplasmataceae strain are given herein above. In a preferred embodiment, the Anaplasmataceae strain is an *Ehrlichia* strain.

The *Ehrlichia* strain may be selected from the group consisting of: *E. canis*, *E. chaffeensis*, *E. ewingii*, *E. muris*, and *E. ruminantium*.

The ntrX gene of the bacterial strain may be deleted or inactivated for example by mutation. Thus, the ntrX gene may be mutated by point mutation, by insertion or by deletion of one or more nucleotides so as to for example interrupting the open reading frame of the ntrX gene.

Techniques of inactivation of a gene are well known from the person skilled in the art. Techniques which may be used to inactivate the ntrX gene, may be for example site directed mutagenesis or homologous recombination. It also includes the use of molecules that trigger preferentially the ntrX gene for inactivation.

The method for producing a vaccine composition may also comprise a step of mixing the attenuated strain with a pharmaceutically acceptable excipient.

The method for producing a vaccine composition according to the invention can also comprise steps conventionally used in the manufacture of the commercially available vaccine composition based on live attenuated strains.

The invention will be further illustrated by the following figures and examples. However, these examples should not be interpreted in any way as limiting the scope of the present invention.

FIGURES

Figure 2:
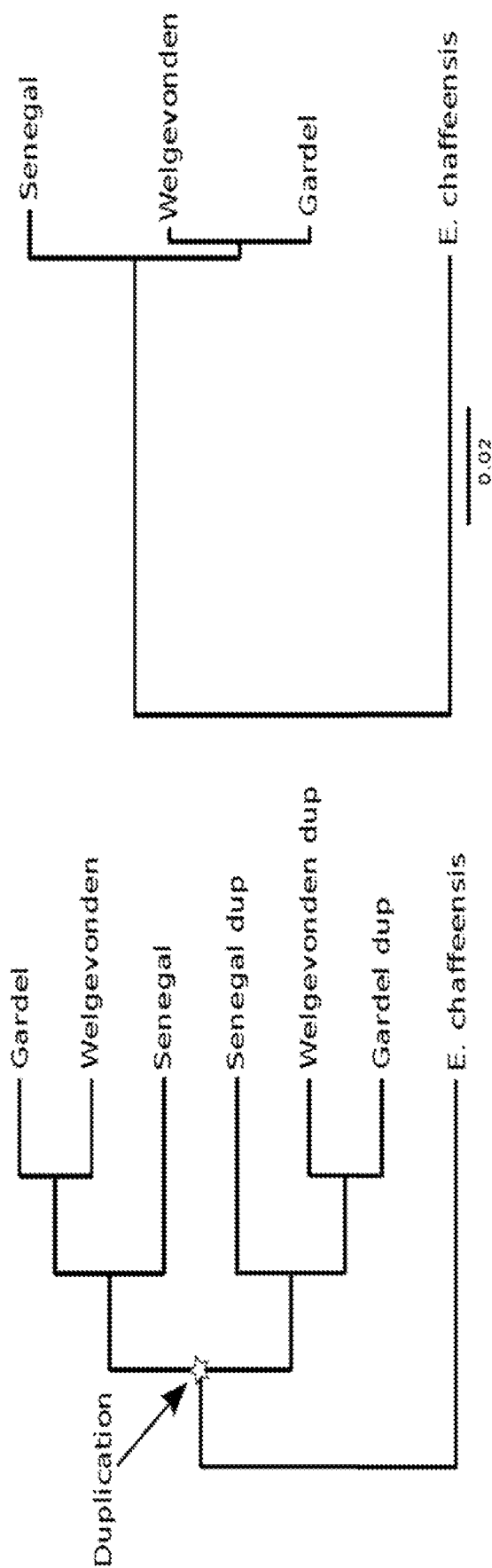

FIGS. 1 and 2 show an evidence of gene conversion between ntrX and its inverted duplicate.

FIG. 1 shows an alignment showing the duplicated region (top four rows) of ntrX gene and the matching parental ntrX region (next four rows) in Welgevonden, Gardel and Senegal virulent and attenuated strains and in *E. chaffeensis* (last row) where there is no inverted duplicate. Alignment positions that show a closer relationship between ntrX and the duplicate within a strain than between strains, including the 4 bp deletion in Senegal strain are bordered by boxes.

FIG. 2 shows a phylogram (left) depicting the expected relationship between ntrX and its duplicate (star) given that it is present in all *E. ruminantium* strains. The structure of the phylogram is based on the interstrain relationship reconstructed in the maximum likelihood phylogeny (right) by concatenating 54 orthologous ribosomal proteins from the strains and *E. chaffeensis*.

EXAMPLES

Material and Methods:
Genomics
DNA Extraction and Purification

*Ehrlichia ruminantium* Senegal strain passage 7 (80% lysis at day 21 p.i.) and 63 and 64 (80% lysis at day 7 p.i.) were cultured in Bovine Aortic endothelial cells as previously described for Gardel strain (Marcelino et al. 2005). When 80% lysis had occurred, supernatant and cellular debris were collected and centrifuged for 15 minutes at 4,000 g at 4° C. to remove cellular debris. The supernatant was then centrifuged for 30 minutes at 20,000 g at 4° C. in order to collect elementary bodies and remove the supernatant. The pellet was resuspended in 2 ml of cold PBS and homogenized gently then 20 ml of PBS was added to wash it, followed by centrifugation for 30 minutes at 20,000 g at 4° C. The pellet was resuspended in 350 µl PBS and 10 µl of RNase at 10 mg/ml (SIGMA, Lyon, France) and 150 µl of DNase I (Roche, Boulogne-Billancourt, France) were added. The pellet was incubated at 37° C. for 90 minutes and the reaction was stopped by adding 25 µl 0.5M EDTA, pH8. The DNase and Rnase were removed by centrifugation for 15 minutes at 20,000 g at 12° C. followed by a wash with 900 µl of sterile DNase and RNase free water. Cells were centrifuged under the same conditions and the washing step was repeated twice. Lysis of elementary bodies was performed by adding 500 µl of lysis solution (0.1M TRIS-HCl (pH8), 0.15M NaCl, 0.025M EDTA (pH8), 1.5% SDS, 0.3 mg/ml Proteinase K) followed by Incubation for 120 minutes at 55° C. DNA extraction was performed using phenol/chloroform (Perez et al. 1997) as follows: 500 µl of phenol (Eurobio, Courtaboeuf, France) was added to 500 µl of sample and mixed gently to homogenize followed by centrifugation for 5 minutes at 8000 g. The aqueous phase was collected and an equivalent volume of phenol was added before centrifugation for 5 minutes at 8,000 g. The aqueous phase was collected and an equivalent volume of phenol (Eurobiotech, France), chloroform and isoamylalcool (Prolabo, Normapur, France) in 24:24:1 proportion was added and mixed gently. The mixture was centrifuged for 5 minutes at 8,000 g and the aqueous phase collected and mixed gently with an equal volume of chroroform/isoamylalcool in 48:1 proportion. The mixture was centrifuged for 5 minutes at 8,000 g and the supernatant was collected and precipitated in ethanol (Prolabo, Normapur) by adding 2 volumes of absolute ethanol for 1 volume of the collected sample. The sample was stored at 4° C. for one hour in order to obtain a white precipitate which was then centrifuged for 10 minutes at 10,000 g at 10° C. The supernatant was removed and the pellet resuspended in 1 ml of 75% ethanol followed by centrifugation for 5 minutes at 10,000 g. The supernatant was removed and the pellet air dried. The pellet was resuspended in 25 µl of TE buffer (10 mM TRISpH8, 1 mM EDTA pH8). DNAs from Senegal passage 7, 63 and 64 in TE buffer were stored at −20° C. before being used for further sequencing.

Genome Sequencing and Assembly

The genome of the virulent Senegal strain (passage 7) was sequenced using 454 GS FLX technology. The attenuated strain (passage 63 & 64) was sequenced using 454 GS FLX technology and Sanger sequencing. Adapters for the 454 sequences were clipped using NextGen Sequence Workbench v3.2.3 ("NextGen Sequence Workbench" 2015), and reads were clipped for adaptors and quality scores according to the information in the SFF sequence files as well as removing reads less than 25 bp long or those with an average quality score less than 16. Quality trimming was performed for the Sanger sequences using NextGen Sequence Workbench v3.2.3 ("NextGen Sequence Workbench" 2015) with default settings (clip the reads in a 14 bp window until >63% have a quality score>=20) and removing reads less than 25 bp long or those with an average quality score less than 16. The virulent strain was de novo assembled using Mira 4.0.2 (Chevreux, Wetter, and Suhai 1999), resulting in 43 contigs larger than 1 kb. The contigs were ordered according to the previously published Welgevonden strain genome (Collins et al. 2005) using CONTIGuator (Galardini et al. 2011), which mapped 42 of the 43 contigs to the Welgevonden genome. The assembly was checked by realigning the reads onto the concatenated assembly using Bowtie 2 (Langmead and Salzberg 2012) and checking any predicted variants against the Welgevonden genome sequence (Collins et al. 2005). Duplicate reads were removed using Picard ("Picard Tools" 2016), conversion between SAM and BAM formats, sorting and mpileup was done using Samtools (Li et al. 2009) and variants were called using BCFtools (Li et al. 2009) and viewed with Tablet (Milne et al. 2013). Variant calls were manually examined in Tablet (Milne et al. 2013) and the assembly was edited accordingly. The attenuated strain was mapped onto the assembled virulent strain as described for remapping the virulent strain. Indels and SNPs were identified with quality cutoffs of 50 and 20 respectively and manually examined in the read alignment. Both genome assemblies were submitted to Genbank (Accessions MQUJ00000000 for *Ehrlichia ruminantium* Senegal Virulent, MRDC00000000 for *Ehrlichia ruminantium* Senegalp63 attenuated).

E. ruminantium RNA Purification for RT-PCR

*E. ruminantium* Senegal attenuated (passage 63 and 66) and virulent (passage 7 and 11) were inoculated in 25 cm² TC flask containing BAE cells as previously described (Marcelino et al. 2005). The medium was changed at 24 h and 72 h for the attenuated strain and at 24 h and every two days, thereafter, for the virulent strain. Cell layers were allowed to reach around 80-90% lysis and were mechanically harvested with a scraper. Re-suspended cells were centrifuged at 4,500×g for 30 minutes at 4° C. Supernatant was discarded and cells were re-suspended in 1 ml PBS. Cells were then centrifuged at 10,000×g for 10 minutes and PBS was removed. Pellets were stored at −70° C. until RNA purification. Cell pellets were allowed to thaw for 5 minutes in ice and RNA was purified using the SV total RNA isolation system (Promega Corporation, Wisconsin, USA). An additional DNAse treatment was added by using the rigorous DNAse treatment with Turbo DNA-free (Ambion, Fisher Scientific, Illkirch, France), which consisted in adding 0.5 µl of the DNAse, incubating for 30 minutes, and repeating this procedure. RNA was immediately stored at −70° C. after inactivation of the DNAse before ntrX RT-PCR.

RT-PCR of ntrX

The expression of the ntrX in the virulent (passage 7 and 11) and attenuated (passage 63 and 66) Senegal strains was determined using the primers ntrX qRT F1 (5'-GGAAA-GATTGTATATTTCTG-3') (SEQ ID NO: 21) and ntrX qRT2 R1 (5'-ACCAGTAATGAGTATACGAC-3') (SEQ ID NO: 22) that amplify a 517 bp piece of the ntrX gene. Amplifications were done using the OneStep RT-PCR kit (QIAgen, California, USA) with the following conditions: one Reverse transcriptase cycle at 50° C. for 30 minutes, a denaturating cycle at 95° C. for 15 minutes for activation of HotStart Taq, 35 cycles with a denaturating step 95° C. for 1 minute, an annealing step at 50° C. for 1 minute, and an amplification step at 72° C. for 1 minute, followed by an amplification cycle of 72° C. for 10 minutes. DNA from *E. ruminantium* Senegal passage 6 was used as positive control. Products were run in agarose gel and bands were visualized with SYBR safe.

Distance of E. Muds and Senegal Strain Intergenic Regions

The Senegal strain genome was aligned to the *Ehrlichia muris* genome using Mauve 2.3.1 (Darling et al. 2004) and intergenic regions were output from the alignment based on the *E. muris* annotation. Distances were calculated between the aligned intergenic regions using the TN93 model (Tamura and Nei 1993) in the APE package (Paradis, Claude, and Strimmer 2004) in R version 3.2.3 (R Core Team 2015) where at least 30 bases could be aligned, resulting in 364 intergenic distances between Senegal strain and *E. muris*. The distance between the ntrX gene from *E. muris* and the duplicate from Senegal strain was measured in the same way for comparison with the intergenic regions.

Vaccination

Preparation of the Inoculum

A. Preparation of the Purified Supernatant

As soon as 80% of lysis of cells is reached with a synchronous infection corresponding to 5 days of culture of Senegal passage 68, the supernatant with the cellular debris was passed in a syringe 26 G3/8. The totality of the supernatant was collected and centrifuged for 15 minutes at 3000 rpm. Then, the supernatant was recovered without removing the cellular pellet.

500 µl of the supernatant was tested in order to evaluate the viability of the sample. One part of the purified supernatant has been used to infect endothelial cell TC flask in order to control the infectivity of the inoculum 14 ml were at 4° C. before inoculation.

B. Evaluation of the Viability Using the LIVE/DEAD BacLight™ Bacterial Viability Kits (ThermoFisher Scientific)

The purified supernatant was washed in 15 ml of physiological serum and then centrifuged 30 min at 20,000 g at 4° C. It has been suspended again in 500 µl of physiological serum, passed in a syringe. 1.5 µl of Syto9 and Propidium Iodide was added. It was incubated 15 min then counted on a slide and passed in a flow cytometer. It was counted in a Neubeaur chamber in triplicate 8 squares each time. The final concentration was obtained by multiplication by the factor $1.6*10^5$. There was no dilution factor.

Infection of the Animals

Naïve goats were injected intravenously with the following doses of elementary bodies of live attenuated Senegal strain passage 64. The calibrated doses which reproduce natural challenge for virulent strain (between 10 and 12 days before hyperthermia and dead between day 12 and 15 after infection) is comprised between $3\times10^4$ an $9\times10^4$ live elementary bodies per goat (Vachiery et al, 2006). For this experiment, we decided to use a lethal dose and ten times the lethal dose using $9\times10^4$ and $9\times10^5$ live elementary bodies per goat.

| Goat number | Challenge Doses (Live elementary body number) |
|---|---|
| 0615 | $9\ 10^4$ |
| 0636 | $9\ 10^4$ |
| 0803 | $9\ 10^5$ |

Preparation of inoculum depending on the viabilities and concentrations which were found.

Viability

From the cell culture supernatant we measured $5.89\times10^6$ elementary bodies/ml on neaubeaur counting cell. The percentage of viability was measured by flow cytometry and we obtained 40% of viability. The number of live elementary bodies was $2.35\times10^6$ CE live/ml. The supernatant was diluted in fresh cell culture medium to get $9\times10^4$ and $9\times10^5$ elementary bodies in a final volume of 2 ml.

Monitoring of Animals;

Clinical signs were checked every day in order to score the severity of the disease. A serology targeting MAP-1 antibodies was done one time a week and one blood sample were taken daily.

Results:

Virulent and Attenuated Senegal Strains Genomic Differences: SNPs and Indels

The variants found between the virulent and attenuated strains are shown in Table below.

TABLE

Days for lysis of virulent and attenuated Senegal strain passages

| Passage | Days to lyse | Virulence |
|---|---|---|
| 4 | 5 | Virulent |
| 4 | 8 | Virulent |
| 4 | >8 | Virulent |
| 4 | >10 | Virulent |
| 5 | 6 | Virulent |
| 5 | >7 | Virulent |
| 5 | 5 | Virulent |
| 6 | 14 | Virulent |
| 6 | 14 | Virulent |
| 6 | >7 | Virulent |
| 6 | 7 | Virulent |
| 6 | >5 | Virulent |
| 7 | 4 | Virulent |
| 7 | 4 | Virulent |
| 7 | 6 | Virulent |
| 7 | 6 | Virulent |
| 8 | 6 | Virulent |
| 8a | 6 | Virulent |
| 8b | 6 | Attenuated |
| 65 | 4 | Attenuated |
| 68 | 5 | Attenuated |
| 69 | 5 | Attenuated |
| 70 | 5 | Attenuated |
| 70 | 4 | Attenuated |
| 71 | 4 | Attenuated |
| 73 | 4 | Attenuated |
| 74 | 4 | Attenuated |
| 74 | 4 | Attenuated |
| 75 | 5 | Attenuated |
| 75 | 4 | Attenuated |
| 76 | 4 | Attenuated |

We identified only two SNPs and three indels between the virulent and attenuated Senegal strains. The SNPs occur in the glyA (ERGA_CDS_07110 ortholog), a serine hydroxymethyltransferase involved in the interconversion of serine and glycine as well as tetrahydrofolate production, and the ERGA_CDS_07720 ortholog, a putative M16 protease. Both SNPs are non-synonymous. The indels occur in a hypothetical gene (ERGA_CDS_01780 ortholog), the response regulator of the putative nitrogen-sensing two-component system, ntrX (ERGA_CDS_06840 ortholog) and map1-2 (ERGA_CDS_09130 ortholog), a member of the map1 family of outer membrane proteins. The hypothetical gene and ntrX both contain a 4 bp deletion, while the map1-2 gene contains a 2 bp insertion. The map1-2 gene appears to be a pseudogene in the virulent Senegal strain and the result of the insertion is to restore the open reading frame of the gene in the attenuated strain, making it a possible gain of function mutation. The hypothetical protein contains a Patatin domain and has sequence similarity to other patatin-like phospholipase family proteins that have lipolytic activity (Banerji and Flieger 2004).

Candidate Mutations for Senegal Strain Attenuation

The two nonsynonymous SNPs and the three indels identified between the virulent and attenuated Senegal strains provide a small number of candidates to explain the attenuation process in this strain.

The glyA gene is involved in the interconversion of serine and glycine, and is necessary for virulence in *Salmonella Typhimurium* and *Brucella* species (Köhler et al. 2002; Xiang, Zheng, and He 2006; Jelsbak et al. 2014). However, the attenuation in *Brucella suis* was obtained by Tn5 insertion to knock out the gene, and in the case of the SNP in our data, the protein is still probably produced. The substituted amino acid lies near the end of the protein (position 388/421) and outside of any predicted domains. An alignment of glyA in several Rickettsial species shows that while most of the protein is well conserved, the portion where the mutation occurs is variable across the species suggesting that the region is not vital for protein function.

The map1-2 gene is a member of a multigene family of Major Antigenic Proteins in the Anaplasmataceae, Pfam PF01617 (Dunning Hotopp et al. 2006), which are surface exposed and have been identified as potential vaccine targets (Bekker et al. 2002). Some members of these map genes have been experimentally characterized as porins (Huang et al. 2007) and are suspected to be involved in host cell adhesion (Garcia-Garcia et al. 2004; Park, Choi, and Dumler 2003). Thus, its mutation appears to be a potential candidate for attenuation. However, a study of the map1-2 gene in several different strains of *E. ruminantium* failed to provide evidence of transcription of this gene in any of the strains they tested (Senegal virulent and attenuated, Gardel, Welgevonden and Sankat 430) in either ticks or bovine endothelial cells (Bekker et al. 2002). A different study did however report the transcription of the map1-2 gene in Welgevonden (van Heerden et al. 2004). The map1-2 gene contains a 2 bp deletion in the Senegal virulent strain (presumably rendering it non-functional) that is reverted in the attenuated strain. Curiously, the deletion is not present in a previous study using a different isolate of the virulent Senegal strain (Bekker et al. 2005). Examination of the reads covering this indel in our data revealed that they fully support the deletion in the virulent Senegal, while it is not present in any reads in the attenuated strain. This result suggests that this deletion may be unique to the virulent strain sequenced in this study. The lack of detectable transcription of the gene in some strains (Bekker et al. 2002) and the fact that the complete map1-2 sequence is present in several other virulent strains of *E. ruminantium* including another Senegal isolate makes the reversion insertion unlikely to be the cause of attenuation of the Senegal strain.

The patatin domain-containing protein (ERGA_CDS_01780 ortholog) may play a role in the virulence of *E. ruminantium*, as patatin-like phospholipase proteins are putatively involved in host cell entry in *Rickettsia* (Rahman et al. 2010). Phospholipase proteins have been identified as virulence factors secreted by the Type III secretion system in *Pseudomonas aeruginosa* (ExoU), and the Type IV-B secretion system in *Legionella* pneumophiHa (VipD) (Rahman et al. 2010). Bacterial pathogens also tend to contain more patatin-like-proteins than non-pathogens (Banerji and Flieger 2004), suggesting possible roles in virulence. However, their presence in non-pathogens also shows that patatins are not always involved in virulence functions. The indel in the attenuated strain is close to, but outside of the predicted patatin domain, suggesting that the phospholipase activity might be maintained, but making the result of the indel unsure in terms of its effect on the function of the protein. Proteolysis can play roles in virulence at various levels in bacterial pathogens (Frees, Brøndsted, and Ingmer 2013), and although we could find no evidence for a known role of proteases from the M16 family in bacterial virulence, proteases from this family in *Toxoplasma gondii* have been suggested to play a possible role in host invasion by the parasite (Laliberté and Carruthers 2011).

Consequently, the only attenuation candidate is the ntrX gene containing the 4 bp deletion because it is the response regulator of one of only three two-component systems in *E. ruminantium* that are responsible for global regulation of various bacterial systems (Cheng et al. 2006; Kumagai et al. 2006; Cheng, Lin, and Rikihisa 2014). Two-component systems are involved in sensing of environmental or cellular signals and the downstream expression of genes, allowing bacteria to coordinate their gene expression in response to their environment or cellular state. During infection, bacterial pathogens need to efficiently coordinate their metabolic activities with their virulence to allow for maximization of their growth and successful attack on the host cells, while avoiding host defences. Signals such as the availability of nutrients or metabolites may inform the bacteria of the optimal time to produce virulence factors, and the regulation of many bacterial virulence factors is linked with nutrient availability (Somerville and Proctor 2009; Barbier, Nicolas, and Letesson 2011). NtrX lies at the crossroads of environmental sensing and gene expression and is therefore the ideal candidate to explain attenuation because perturbations to the NtrY/X system are likely to have major consequences for the growth, survival and the coordination of bacterial metabolism and virulence. Furthermore, ntrX as the attenuator explains the apparently biased nature of attenuation in the Senegal strain as compared to other *E. ruminantium* strains due to its genomic context, which will be discussed later.

The ntrX Gene is Disrupted by Segmental Gene Conversion from a Nearby Inverted Partial ntrX Duplication in Attenuated Senegal Strain A segment of the ntrX gene has been duplicated in all *E. ruminantium* genomes for which there is available genome sequence data. The duplicated section is inverted and covers 421 bp close to the 5' end of ntrX (not including the start codon), and lies roughly 2 kb downstream of the ntrX gene itself. The alignment between the ntrX and the duplicate region reveals that the 4 bp deletion identified in the ntrX gene in the Senegal attenuated strain is also present in the duplicated segment in both the attenuated and virulent strains of Senegal, but not in any of the other strains. The 4 bp deletion in ntrX in the attenuated strain causes a frameshift between the domain regions for the response regulator receiver domain and the sigma factor interaction domain, which introduces a stop codon that disrupts the gene. There are also seven other mutations across the sequenced strains between ntrX and its duplicate that exhibit a pattern that is incongruent with the expected phylogeny. At these residues, the ntrX gene and its duplicate are more similar within a strain than they are to their orthologous positions in the other strains, a pattern that indicates gene conversion (FIGS. 1 and 2).

| | SEQ ID NO: | Nucleic acid sequences of regions shown at figure 1 |
|---|---|---|
| Welgevonden Duplicate | 12 | CTAATAATGATATATTAGGTGTGATAATTATATCACTAAATTAGCAGTTGATGGTTTATCCGCGATCAAGATG GCTTATGAAAAAGAGCCTGATGTTGTATTATTGGATATATGGTTAAGAGGATCTGATATTGATGGATTAAGT GTACTGGAAAAGCTTAAAGAAAGGTATCCTTATTTGCCTGTTATTATGATTAGTGGGCATGGTAATATTGCCA CTGCTGTAAAGTCTCTGCATATGGGTGCTTATGATTATATAGAAAAGCCTTTTACAGAAGGAAGATTAAAGT TAGTTGTAAAGAGAGCTATAGAGTCTGGTAGATTACGTAGAGAAAATGATGAGTTGAAATCAGCATTTGAG GATTATGAAATAGTCGGTAACTCCCCTGTTATACGTAATTTGAGAAGTATGGTTAATAA |
| Gardel Duplicate | 13 | CTAATAATGATATATTAAGTGATGATAATTATGTCACTAAATTAGCAGTTGATGGTTTATCCGCGATCAAGAT GGCTTATGAAAAAGAGCCTGATGTTGTATTATTGGATATATGGTTAAGAGGATCTGATATTGATGGATTAAG TGTACTGGAGAAGCTTAAAGAAAGGTATCCTTATTTGCCTGTTATTATGATTAGTGGGCATGGTAATATTGCC ACTGCTGTAAAGTCTCTGCATATGGGTGCTTATGATTATATAGAAAAGCCTTTTACAGAAGGAAGATTAAAG TTAGTTGTAAAGAGAGCTATAGAGTCTGGTAGATTACGTAGAGAAAATGATGAGTTGAAATCAGCATTTGAG GATTATGAAATAGTCGGTAACTCCCCTGTTATACGTAATTTGAGAAGTATGATTAATAA |
| Senegal Virulent Duplicate | 14 | CTAATAATGATATATTAGGCAATGATAATTATGTAACCAAATTAGCAGTTGATTATTTATGAAAAAGAGCCTG ATGTTGTATTATTGGATATATAGTTAAAGAGGATCTGATATTGATGGATTAAGCGTACTGGAAAAGCTTAAA GAAAGGTATCCTTATTTGCCTGTTATTATGATTAGTGGGCATGGTAATATTGCTACTGCTGTAAAGTCTTTGC ATATGGGTGCTTATGATTATATAGAAAAGCCTTTTACAGAAGGAAGATTAAAGTTGTAAAGAGAGCTATAGA |

| SEQ ID NO: | Nucleic acid sequences of regions shown at figure 1 |
|---|---|
| | GTCTGGTAGATTACGTAGAGAAAATGATGAGTTGAAATCAGCATTTGAGGATTATGAGATAGTGGGTAACTC<br>GCCTGTTATACGTAATTTGAGAAGTATGATTAATAA |
| Senegal Attenuated Duplicate    15 | CTAATAATGATATATTAGGCAATGATAATTATGTAACCAAATTAGCAGTTGATTATTTATGAAAAAGAGCCTG<br>ATGTTGTATTATTGGATATATAGTTAAAGAGGATCTGATATTGATGGATTAAGCGTACTGGAAAAGCTTAAA<br>GAAAGGTATCCTTATTTGCCTGTTATTATGATTAGTGGGCATGGTAATATTGCTACTGCTGTAAAGTCTTTGC<br>ATATGGGTGCTTATGATTATATAGAAAAGCCTTTTACAGAAGGAAGATTAAAGTTGTAAAGAGAGCTATAGA<br>GTCTGGTAGATTACGTAGAGAAAATGATGAGTTGAAATCAGCATTTGAGGATTATGAGATAGTGGGTAACTC<br>GCCTGTTATACGTAATTTGAGAAGTATGATTAATAA |
| Welgevonden ntrX    16 | CTAATAAAAGATATATTAAGTGATGATAATTATGTCACTAAATTAGCAGTTGATGGTTTATCCGCGATCAAGA<br>TGGCTTATGAAAAAGAGCCTGATGTTGTATTATTAGATATATGGTTAAGAGGATCTGATATTGATGGATTAAG<br>TGTACTGGAAAAGCTTAAAGAAAGGTATCCTTATTTGCCTGTTATTATGATTAGTGGGCATGGTAATATTGCC<br>ACTGCTGTAAAGTCTCTGCATATGGGTGCTTATGATTATATAGAAAAGCCTTTTACAGAAGGAAGATTAAAG<br>TTAGTTGTAAAGAGAGCTATAGAGTCTGGTAGATTACGTAGAGAAAATGATGAGTTGAAATCAGCATTTGAG<br>GATTATGAAATAGTCGGTAACTCCCCTGTTATACGTAATTTGAGAAGTATGATTAATAA |
| Gardel ntrX    17 | CTAATAAAAGATATATTAAGTGATGATAATTATGTCACTAAATTAGCAGTTGATGGTTTATCCGCGATCAAGA<br>TGGCTTATGAAAAAGAGCCTGATGTTGTATTATTGGATATATGGTTAAGAGGATCTGATATTGATGGATTAA<br>GTGTACTGGAGAAGCTTAAAGAAAGGTATCCTTATTTGCCTGTTATTATGATTAGTGGGCATGGTAATATTGC<br>CACTGCTGTAAAGTCTCTGCATATGGGTGCTTATGATTATATAGAAAAGCCTTTTACAGAAGGAAGATTAAA<br>GTTAGTTGTAAAGAGAGCTATAGAGTCTGGTAGATTACGTAGAGAAAATGATGAGTTGAAATCAGCATTTGA<br>GGATTATGAAATAGTCGGTAACTCCCCTGTTATACGTAATTTGAGAAGTATGATTAATAA |
| Senegal Virulent ntrX    18 | CTAATAAAAGATATATTAAGTGATGATAATTATGTCACTAAATTAGCAGTTGATGGTTTATCTGCGATCAAGA<br>TGGCTTATGAAAAAGAGCCTGATGTTGTATTATTGGATATATGGTTAAGAGGATCTGATATTGATGGATTAA<br>GCGTACTGGAAAAGCTTAAAGAAAGGTATCCTTATTTACCTGTTATTATGATTAGTGGGCATGGTAATATTGC<br>TACTGCTGTAAAGTCTTTGCATATGGGTGCTTATGATTATATAGAAAAGCCTTTTACAGAAGGAAGATTAAA<br>GTTAGTTGTAAAGAGAGCTATAGAGTCTGGTAGATTACGTAGAGAAAATGATGAGTTGAAATCAGCATTTGA<br>GGATTATGAGATAGTGGGTAACTCGCCTGTTATACGTAATTTGAGAAGTATGATTAATAA |
| Senegal Attenuated ntrX    19 | CTAATAAAAGATATATTAAGTGATGATAATTATGTCACTAAATTAGCAGTTGATGGTTTATCTGCGATCAAGA<br>TGGCTTATGAAAAAGAGCCTGATGTTGTATTATTGGATATATGGTTAAGAGGATCTGATATTGATGGATTAA<br>GCGTACTGGAAAAGCTTAAAGAAAGGTATCCTTATTTACCTGTTATTATGATTAGTGGGCATGGTAATATTGC<br>TACTGCTGTAAAGTCTTTGCATATGGGTGCTTATGATTATATAGAAAAGCCTTTTACAGAAGGAAGATTAAA<br>GTTGTAAAGAGAGCTATAGAGTCTGGTAGATTACGTAGAGAAAATGATGAGTTGAAATCAGCATTTGAGGA<br>TTATGAGATAGTGGGTAACTCGCCTGTTATACGTAATTTGAGAAGTATGATTAATAA |
| E. chaffeensis ntrX    20 | TTAATAAAGGATATATTAAGTGATGATAATTATGTCACAAAATTAGCAGTTGATGGGTTGTCTGCTATTAAGA<br>TGGCTTATGAGAAAGAACCAGATGTTGTTTTACTAGATATATGGTTAAAAGGATCAGATATTGATGGGTTAA<br>GTGTTTTAGAGAAACTAAAGGAAAGGTATCCATATTTACCTGTGATTATGATTAGTGGACATGGTAATATTGC<br>TACTGCTGTGAAGTCTTTGCACATGGGAGCTTATGATTATATAGAGAAACCTTTTACAGAAGGTAGATTAAA<br>GTTAGTAGTTAAGAGAGCGATAGAATCTGGTAGATTGCGTAGAGAAAATGACGAATTAAAATCAACATTTGA<br>AGATTACGAAATAGTTGGCAACTCTCCTGTAATAAAAAATCTAAGGAGTATGATTAATAA |

NtrX is Expressed in Senegal Virulent Strain but not in the Attenuated Strain

To confirm the pseudogenisation of ntrX in the attenuated strain, we performed a RT-PCR on RNA samples from the virulent (passage 7 and 11) and avirulent (passage 63 and 66) strains. RT-PCR resulted in the amplification of a 517 bp in one (Senegal passage 11 and not Senegal passage 7) of the two virulent samples confirming the expression of ntrX. No band was observed in either of the samples from the attenuated strain indicating that ntrX gene is not expressed in the attenuated Senegal strain.

Vaccination with the Attenuated Strain

After inoculation, the goats infected with the attenuated strain suffered from a slight hyperthermia with no other clinical signs and all survived even with 10-fold lethal dose of challenge. Consequently, the mutant *E. ruminantium* passage 64 is attenuated.

100% of goats infected with the attenuated strain and which were submitted to a challenge with the virulent strain (*E. ruminantium* passage 7) survived, whereas all the control goats, which were submitted to a challenge with the virulent strain without having been previously infected with the attenuated strain, died.

These results show that a *E. ruminantium* with an inactive or deleted ntrX gene provides an efficient vaccine against ehrlichiosis.

Owing to the very high conservation degree of the ntrX gene in the Anaplasmataceae family (see table 1), these results apply to the other strains of the Anaplasmataceae family.

REFERENCES

Throughout this application, various references describe the state of the art to which this invention pertains. The disclosures of these references are hereby incorporated by reference into the present application.

Atack, John M., Yogitha N. Srikhanta, Karrera Y. Djoko, Jessica P. Welch, Norain H. M. Hasri, Christopher T. Steichen, Rachel N. Vanden Hoven, et al. 2013. "Characterization of an ntrX Mutant of *Neisseria gonorrhoeae* Reveals a Response Regulator That Controls Expression of Respiratory Enzymes in Oxidase-Positive Proteobacteria." Journal of Bacteriology 195 (11): 2632-41. doi: 10.1128/JB.02062-12.

Banerji, Sangeeta, and Antje Flieger. 2004. "Patatin-like Proteins: A New Family of Lipolytic Enzymes Present in Bacteria?" Microbiology (Reading, England) 150 (Pt 3): 522-25. doi: 10.1099/mic.0.26957-0.

Bekker, Cornells P. J., Lesley Bell-Sakyi, Edith A. Paxton, Dominique Martinez, Albert Bensaid, and Frans Jongejan.

2002. "Transcriptional Analysis of the Major Antigenic Protein 1 Multigene Family of *Cowdria ruminantium*." Gene 285 (1-2): 193-201.

Bekker, Cornells P. J., Milagros Postigo, Amar Taoufik, Lesley Bell-Sakyi, Conchita Ferraz, Dominique Martinez, and Frans Jongejan. 2005. "Transcription Analysis of the Major Antigenic Protein 1 Multigene Family of Three In Vitro-Cultured *Ehrlichia ruminantium* Isolates." Journal of Bacteriology 187 (14): 4782-91. doi: 10.1128/JB.187.14.4782-4791.2005.

Camus, E., and N. Barre. 1988. "[Diagnosis of headwater from brain ecrasement]." Revue Cheng, Zhihui, Yumi Kumagai, Mingqun Lin, Chunbin Zhang, and Yasuko Rikihisa. 2006. "Intra-Leukocyte Expression of Two-Component Systems in *Ehrlichia Chaffeensis* and *Anaplasma Phagocytophilum* and Effects of the Histidine Kinase Inhibitor Closantel." Cellular Microbiology 8 (8): 1241-52. doi:10.1111/j.1462-5822.2006.00704.x.

Cheng, Zhihui, Mingqun Lin, and Yasuko Rikihisa. 2014. "*Ehrlichia Chaffeensis* Proliferation Begins with NtrY/NtrX and PutA/GlnA Upregulation and CtrA Degradation Induced by Proline and Glutamine Uptake." mBio 5 (6). doi: 10.1128/mBio.02141-14.

Chevreux, B., T. Wetter, and S. Suhai. 1999. "Genome Sequence Assembly Using Trace Signals and Additional Sequence Information." In Proceedings of the German Conference on Bioinformatics, 99:45-56.

Collins, Nicola E., Junita Liebenberg, Etienne P. de Villiers, Kelly A. Brayton, Elmarié Louw, Alri Pretorius, F. Erika Faber, et al. 2005. "The Genome of the Headwater Agent *Ehrlichia ruminantium* Contains Multiple Tandem Repeats of Actively Variable Copy Number." Proceedings of the National Academy of Sciences of the United States of America 102 (3): 838-43. doi:10.1073/pnas.0406633102.

Darling, Aaron C. E., Bob Mau, Frederick R. Blattner, and Nicole T. Perna. 2004. "Mauve: Multiple Alignment of Conserved Genomic Sequence with Rearrangements." Genome Research 14 (7): 1394-1403. doi:10.1101/gr.2289704.

Dunning Hotopp, Julie C., Mingqun Lin, Ramana Madupu, Jonathan Crabtree, Samuel V. Angiuoli, Jonathan A. Eisen, Jonathan Eisen, et al. 2006. "Comparative Genomics of Emerging Human Ehrlichiosis Agents." PLoS Genetics 2 (2): e21. doi: 10.1371/journal.pgen.0020021.

Frees, Dorte, Lone Brandsted, and Hanne Ingmer. 2013. "Bacterial Proteases and Virulence." Sub-Cellular Biochemistry 66: 161-92. doi:10.1007/978-94-007-5940-4_7.

Frutos, Roger, Alain Viari, Conchita Ferraz, Anne Morgat, Sophie Eychenie, Yane Kandassamy, Isabelle Chantal, et al. 2006. "Comparative Genomic Analysis of Three Strains of *Ehrlichia ruminantium* Reveals an Active Process of Genome Size Plasticity." Journal of Bacteriology 188 (7): 2533-42. doi: 10.1128/JB.188.7.2533-2542.2006.

Galardini, Marco, Emanuele G. Biondi, Marco Bazzicalupo, and Alessio Mengoni. 2011. "CONTIGuator: A Bacterial Genomes Finishing Tool for Structural Insights on Draft Genomes." Source Code for Biology and Medicine 6: 11. doi: 10.1186/1751-0473-6-11.

Garcia-Garcia, Jose C., José de la Fuente, Gianna Bell-Eunice, EdmourF. Blouin, and Katherine M. Kocan. 2004. "Glycosylation of *Anaplasma* Marginale Major Surface Protein 1a and Its Putative Role in Adhesion to Tick Cells." Infection and Immunity 72 (5): 3022-30. doi: 10.1128/IAI.72.5.3022-3030.2004.

Jansen, Gunther, Lena L. Crummenerl, Felix Gilbert, Timm Mohr, Roxana Pfefferkorn, Robert Thänert, Philip Rosenstiel, and Hinrich Schulenburg. 2015. "Evolutionary Transition from Pathogenicity to Commensalism: Global Regulator Mutations Mediate Fitness Gains through Virulence Attenuation." Molecular Biology and Evolution 32 (11): 2883-96. doi: 10.1093/molbev/msv160.

Jelsbak, Lotte, Hassan Hartman, Casper Schroll, Jesper T. Rosenkrantz, Sebastien Lemire, Inke Wallrodt, Line E. Thomsen, et al. 2014. "Identification of Metabolic Pathways Essential for Fitness of *Salmonella Typhimurium* In Vivo." PLoS ONE 9 (7): e101869. doi:10.1371/journal.pone.0101869.

Jongejan, F. 1991. "Protective Immunity to Headwater (*Cowdria ruminantium* Infection) Is Acquired after Vaccination with in Vitro-Attenuated Rickettsiae." Infection and Immunity 59 (2): 729-31.

Köhler, Stephan, Vincent Foulongne, Safia Ouahrani-Bettache, Gisèle Bourg, Jacques Teyssier, Michel Ramuz, and Jean-Pierre Liautard. 2002. "The Analysis of the Intramacrophagic Virulome of *Brucella Suis* Deciphers the Environment Encountered by the Pathogen inside the Macrophage Host Cell." Proceedings of the National Academy of Sciences of the United States of America 99 (24): 15711-16. doi: 10.1073/pnas.232454299.

Kumagai, Yumi, Zhihui Cheng, Mingqun Lin, and Yasuko Rikihisa. 2006. "Biochemical Activities of Three Pairs of *Ehrlichia Chaffeensis* Two-Component Regulatory System Proteins Involved in Inhibition of Lysosomal Fusion." Infection and Immunity 74 (9): 5014-22. doi: 10.1128/IAI.00735-06.

Laliberté, Julie, and Vern B. Carruthers. 2011. "*Toxoplasma Gondii* Toxolysin 4 is an Extensively Processed Putative Metalloproteinase Secreted from Micronemes." Molecular and Biochemical Parasitology 177 (1): 49-56. doi: 10.1016/j.molbiopara.2011.01.009.

Langmead, Ben, and Steven L. Salzberg. 2012. "Fast Gapped-Read Alignment with Bowtie 2." Nature Methods 9 (4): 357-59. doi: 10.1038/nmeth. 1923.

Li, Heng, Bob Handsaker, Alec Wysoker, Tim Fennell, Jue Ruan, Nils Homer, Gabor Marth, Goncalo Abecasis, Richard Durbin, and 1000 Genome Project Data Processing Subgroup. 2009. "The Sequence Alignment/Map Format and SAMtools." Bioinformatics (Oxford, England) 25 (16): 2078-79. doi:10.1093/bioinformatics/btp352.

Marcelino, Isabel, Celia Verissimo, Marcos F. Q. Sousa, Manuel J. T. Carrondo, and Paula M. Alves. 2005. "Characterization of *Ehrlichia ruminantium* Replication and Release Kinetics in Endothelial Cell Cultures." Veterinary Microbiology 110 (1-2): 87-96. doi:10.1016/j.vetmic.2005.07.012.

Milne, Iain, Gordon Stephen, Micha Bayer, Peter J. A. Cock, Leighton Pritchard, Linda Cardie, Paul D. Shaw, and David Marshall. 2013. "Using Tablet for Visual Exploration of Second-Generation Sequencing Data." Briefings in Bioinformatics 14 (2): 193-202. doi: 10.1093/bib/bbs012.

Nene, Vishvanath, and Chittaranjan Kole. 2008. Genome Mapping and Genomics in Animal-Associated Microbes. Springer Science & Business Media.

Park, Jinho, Kyoung Seong Choi, and J. Stephen Dumler. 2003. "Major Surface Protein 2 of *Anaplasma Phagocytophilum* Facilitates Adherence to Granulocytes." Infection and Immunity 71 (7): 4018-25. doi:10.1128/IAI.71.7.4018-4025.2003.

Parkinson, J. S., and E. C. Kofoid. 1992. "Communication Modules in Bacterial Signaling Proteins." Annual Review of Genetics 26: 71-112. doi: 10.1146/annurev.ge.26.120192.000443.

Paradis, Emmanuel, Julien Claude, and Korbinian Strimmer. 2004. "APE: Analyses of Phylogenetics and Evolution in R Language." Bioinformatics 20 (2): 289-90. doi: 10.1093/bioinformatics/btg412.

Pilet, Héloïse, Nathalie Vachiéry, Moez Berrich, Rim Bouchouicha, Benoît Durand, Ludovic Pruneau, Valérie Pinarello, et al. 2012. "A New Typing Technique for the Rickettsiales Ehrlichia ruminantium: Multiple-Locus Variable Number Tandem Repeat Analysis." Journal of Microbiological Methods 88 (2): 205-11. doi:10.1016/j.mimet.2011.11.011.

Rahman, M. Sayeedur, Nicole C. Ammerman, Khandra T. Sears, Shane M. Ceraul, and Abdu F. Azad. 2010. "Functional Characterization of a Phospholipase A2 Homolog from Rickettsia Typhi." Journal of Bacteriology 192 (13): 3294-3303. doi: 10.1128/JB.00155-10.

Tanner, Jennifer R., Laam Li, Sebastien P. Faucher, and Ann Karen C. Brassinga. 2016. "The CpxRA Two-Component System Contributes to Legionella Pneumophila Virulence." Molecular Microbiology, March, n/a-n/a. doi: 10.1111/mmi. 13365.

Tamura, K., and M. Nei. 1993. "Estimation of the Number of Nucleotide Substitutions in the Control Region of Mitochondrial DNA in Humans and Chimpanzees." Molecular Biology and Evolution 10 (3): 512-26.

Vachiery N., Lefrançois, T., Esteves, I., Molia, S., Sheikboudou, C., Kandassamy Y., Martinez, D., Optimisation of the inactivated vaccine dose against headwater and in vitro quantification of Ehrlichia ruminantium challenge material. 2006. Vaccine, 24: 4747-4756.

Van Heerden H1, Steyn H C, Allsopp M T, Zweygarth E, Josemans A I, Allsopp B A. 2004 "Characterization of the pCS20 region of different Ehrlichia ruminantium isolates." Vet Microbiol. 101 (4):279-91.

Xiang, Zuoshuang, Wenjie Zheng, and Yongqun He. 2006. "BBP: Brucella Genome Annotation with Literature Mining and Curation." BMC Bioinformatics 7: 347. doi: 10.1186/1471-2105-7-347.

Zweygarth, Erich, Antoinette I. Josemans, M. Fransie Van Strijp, Laura Lopez-Rebollar, Mirinda Van Kleef, and Basil A. Allsopp. 2005. "An Attenuated Ehrlichia ruminantium (Welgevonden Stock) Vaccine Protects Small Ruminants against Virulent Headwater Challenge." Vaccine 23 (14): 1695-1702. doi: 10.1016/j.vaccine.2004.09.030.

The invention claimed is:

1. A vaccine composition comprising a bacterial strain selected from the group consisting of an *Ehrlichia* strain, an *Anaplasma* strain, a *Rickettsia* strain, an *Orientia* strain, a *Bartonella* strain, and a *Brucella* strain, with a deleted or inactive ntrX gene.

2. The vaccine composition according to claim 1, wherein said ntrX gene:
encodes a NtrX protein having the amino acid sequence of SEQ ID NO: 1
or
is an active homologue thereof encoding a NtrX protein having an amino acid sequence with at least 50% of identity with SEQ ID NO: 1.

3. The vaccine composition according to claim 1 wherein:

the inactive ntrX gene is an inactive mutant:

of a ntrX gene encoding a NtrX protein having the amino acid sequence of SEQ ID NO: 1 or of an active homologue thereof encoding a NtrX protein having an amino acid sequence with at least 50% of identity with SEQ ID NO: 1;

or the ntrX gene which is:

a ntrX gene encoding a NtrX protein having the amino acid sequence of SEQ ID NO: 1 or an active homologue thereof encoding a NtrX protein having an amino acid sequence with at least 50% of identity with SEQ ID NO: 1 is deleted.

4. The vaccine composition according to claim 1 wherein:

the inactive ntrX gene is an inactive mutant of a ntrX gene encoding a NtrX protein having the amino acid sequence selected from the group consisting of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, and SEQ ID NO: 10 or the ntrX gene encoding a NtrX protein having the amino acid sequence selected from the group consisting of SEQ ID NOT, SEQ ID NO:2, SEQ ID NO:3, SEQ ID NO:4, SEQ ID NO:5, SEQ ID NO:6, SEQ ID NO:7, SEQ ID NO:8, SEQ ID NO:9, and SEQ ID NO: 10 is deleted.

5. The vaccine composition according to claim 1, wherein said vaccine composition further comprises a pharmaceutically acceptable excipient.

6. The vaccine composition according to claim 1, wherein the bacterial strain is an Alphaproteobacteria strain.

7. The vaccine composition according to claim 1, wherein the bacterial strain is an *Ehrlichia* strain.

8. The vaccine composition according claim 1, wherein the bacterial strain is selected from the group consisting of: *E. canis, E. chaffeensis, E. ewingii, E. muris*, and *E. ruminantium.*

9. A method for producing a vaccine composition for use against a bacterial strain selected from the group consisting of an *Ehrlichia* strain, an *Anaplasma* strain, a *Rickettsia* strain, an *Orientia* strain, a *Bartonella* strain, and a *Brucella* strain, the method comprising:

inactivating or deleting the ntrX gene of the bacterial strain, thereby obtaining an attenuated bacterial strain.

10. The method for producing a vaccine composition according to claim 9, wherein the bacterial strain is an *Ehrlichia* strain.

11. The method for producing a vaccine composition according to claim 9, wherein the bacterial strain is selected from the group consisting of: *E. canis, E. chaffeensis, E. ewingii, E. muris*, and *E. ruminantium.*

12. A method of inducing an immune response against a bacterial strain, comprising administering the vaccine composition of claim 1 to a subject in need thereof.

13. The method of claim 12, wherein administering the vaccine composition prevents and/or treats an infection caused by the bacterial strain.

14. The method of claim 12, wherein the bacterial strain is an *Ehrlichia* strain and the infection caused by the bacterial strain is ehrlichiosis.

* * * * *

UNITED STATES PATENT AND TRADEMARK OFFICE
CERTIFICATE OF CORRECTION

PATENT NO. : 11,065,321 B2  
APPLICATION NO. : 16/648583  
DATED : July 20, 2021  
INVENTOR(S) : D. Meyer et al.

Page 1 of 1

It is certified that error appears in the above-identified patent and that said Letters Patent is hereby corrected as shown below:

In the Claims

| Column | Line | |
|---|---|---|
| 56 | 39 | change "ID NOT" to -- ID NO: 1 -- |

Signed and Sealed this  
Thirtieth Day of August, 2022

Katherine Kelly Vidal  
*Director of the United States Patent and Trademark Office*